US012575823B2

(12) United States Patent
Murdeshwar et al.

(10) Patent No.: US 12,575,823 B2
(45) Date of Patent: Mar. 17, 2026

(54) ELECTRIC SUTURING DEVICES FOR ENDOSCOPY AND LAPAROSCOPY

(71) Applicant: GYRUS ACMI, INC., Westborough, MA (US)

(72) Inventors: Nikhil M. Murdeshwar, Maple Grove, MN (US); Thomas J. Holman, Princeton, MN (US); Jordan N. Milford, Bethlehem, PA (US)

(73) Assignee: Gyrus ACMI, Inc., Westborough, MA (US)

( * ) Notice: Subject to any disclaimer, the term of this patent is extended or adjusted under 35 U.S.C. 154(b) by 389 days.

(21) Appl. No.: 18/548,427

(22) PCT Filed: Feb. 28, 2022

(86) PCT No.: PCT/US2022/070864

§ 371 (c)(1),
(2) Date: Aug. 30, 2023

(87) PCT Pub. No.: WO2022/187795

PCT Pub. Date: Sep. 9, 2022

(65) Prior Publication Data

US 2024/0130724 A1     Apr. 25, 2024
US 2024/0225634 A9     Jul. 11, 2024

Related U.S. Application Data

(60) Provisional application No. 63/216,638, filed on Jun. 30, 2021, provisional application No. 63/155,072, filed on Mar. 1, 2021.

(51) Int. Cl.
*A61B 17/04*     (2006.01)
*A61B 34/00*     (2016.01)
*A61B 17/00*     (2006.01)

(52) U.S. Cl.
CPC .......... *A61B 17/0469* (2013.01); *A61B 34/73* (2016.02); *A61B 2017/00296* (2013.01);
(Continued)

(58) Field of Classification Search
CPC ................ A61B 17/0469; A61B 34/73; A61B 2034/731; A61B 2017/00296; A61B 2017/00398
See application file for complete search history.

(56) References Cited

U.S. PATENT DOCUMENTS 5,143,054 A     9/1992  Adair
5,217,001 A     6/1993  Nakao et al.
(Continued)

FOREIGN PATENT DOCUMENTS

CN     116916806 A     10/2023
CN     117042700 A     11/2023
(Continued)

OTHER PUBLICATIONS

"Japanese Application Serial No. 2023-553086, Response filed May 23, 2025 to Final Notification of Reasons for Refusal mailed Jan. 7, 2025", w Machine English Translation, 11 pgs.
(Continued)

*Primary Examiner* — Phong Son H Dang
(74) *Attorney, Agent, or Firm* — Schwegman Lundberg & Woessner, P.A.

(57) ABSTRACT

An electromagnetic suturing device comprises a body, a coil in the body and a suturing element actuatable by a magnetic suturing track extending into the first end face, a second arm having a second end face opposing the first end face, a second suturing track extending into the second end face, a coil in the first arm, and a suturing element drivable by a magnetic field generated by the coil to move from the first suturing track to the second suturing track. An electro-
(Continued)

magnetic hammer suturing device comprises a housing and a coil in the housing, a shuttle to reciprocate in the housing by an electromagnetic field generated by the coil and a suturing element to be actuated by the shuttle.

30 Claims, 18 Drawing Sheets

(52) U.S. Cl.
CPC ............... *A61B 2017/00398* (2013.01); *A61B 2034/731* (2016.02)

(56) References Cited

U.S. PATENT DOCUMENTS

| | | | |
|---|---|---|---|
| 5,503,616 | A | 4/1996 | Jones |
| 6,719,763 | B2 | 4/2004 | Chung et al. |
| 6,929,601 | B2 | 8/2005 | Nakao |
| 6,997,931 | B2 | 2/2006 | Sauer et al. |
| 8,123,764 | B2 * | 2/2012 | Meade .................... A61B 34/30 |
| | | | 606/139 |
| 8,696,550 | B2 | 4/2014 | Surti |
| 9,962,155 | B2 | 5/2018 | Meade et al. |
| 2010/0280530 | A1 * | 11/2010 | Hashiba ................. A61B 1/018 |
| | | | 606/144 |
| 2011/0152891 | A1 * | 6/2011 | McLawhorn ...... A61B 17/0625 |
| | | | 606/144 |
| 2011/0251458 | A1 | 10/2011 | Terliuc et al. |
| 2012/0157772 | A1 | 6/2012 | James |
| 2019/0374218 | A1 | 12/2019 | Ostrovsky et al. |
| 2020/0165905 | A1 | 5/2020 | Gooneratne et al. |
| 2020/0352557 | A1 | 11/2020 | Meade et al. |
| 2021/0204934 | A1 * | 7/2021 | Huntington ........ A61B 17/0469 |
| 2021/0282766 | A1 | 9/2021 | Aravalli Avvln et al. |
| 2024/0164623 | A1 | 5/2024 | Milford et al. |

FOREIGN PATENT DOCUMENTS

| | | | |
|---|---|---|---|
| DE | 112022001308 | T5 | 12/2023 |
| DE | 112022001316 | T5 | 12/2023 |
| JP | S59154416 | A | 9/1984 |
| JP | H07178100 | A | 7/1995 |
| JP | 2005318957 | A | 11/2005 |
| JP | 2007503948 | A | 3/2007 |
| JP | 2008513144 | A | 5/2008 |
| JP | 2008540041 | A | 11/2008 |
| JP | 2009524491 | A | 7/2009 |
| JP | 2011517972 | A | 6/2011 |
| JP | 2012532639 | A | 12/2012 |
| JP | 2013514866 | A | 5/2013 |
| JP | 2019505266 | A | 2/2019 |
| JP | 2020501746 | A | 1/2020 |
| JP | 7708870 | | 7/2025 |
| JP | 7719198 | | 7/2025 |
| WO | 2011140118 | | 11/2011 |
| WO | WO-2020165905 | A1 | 8/2020 |
| WO | WO-2022187795 | A1 | 9/2022 |
| WO | WO-2022187800 | A1 | 9/2022 |
| WO | WO-2022187800 | A4 | 9/2022 |

OTHER PUBLICATIONS

"Japanese Application Serial No. 2023-553085, Response filed Jun. 5, 2025 to Final Notification of Reasons for Rejection mailed Jan. 7, 2025", W English Claims, 17 pgs.

"Indian Application Serial No. 202347056489, First Examination Report mailed Aug. 19, 2025", 7 pgs.

"Indian Application Serial No. 202347056697, First Examination Report mailed Aug. 14, 2025", 9 pgs.

"Japanese Application Serial No. 2023-553085, Final Notification of Reasons for Rejection mailed Jan. 7, 2025", W English Translation, 4 pgs.

"Japanese Application Serial No. 2023-553086, Final Notification of Reasons for Refusal mailed Jan. 7, 2025", w English translation, 5 pgs.

U.S. Appl. No. 18/548,523, filed Aug. 31, 2023, Endoscope With Reinsertion Sheath and Suturing Device.

"International Application Serial No. PCT/US2022/070864, International Search Report mailed Aug. 16, 2022", 6 pgs.

"International Application Serial No. PCT/US2022/070864, Invitation to Pay Additional Fees mailed Jun. 24, 2022", 10 pgs.

"International Application Serial No. PCT/US2022/070864, Written Opinion mailed Aug. 16, 2022", 11 pgs.

"International Application Serial No. PCT/US2022/070870, International Search Report mailed Jul. 18, 2022", 7 pgs.

"International Application Serial No. PCT/US2022/070870, Invitation to Pay Additional Fees mailed May 27, 2022", 13 pgs.

"International Application Serial No. PCT/US2022/070870, Written Opinion mailed Jul. 18, 2022", 11 pgs.

"U.S. Appl. No. 18/548,523, Preliminary Amendment filed Aug. 31, 2023", 7 pgs.

"German Application Serial No. 112022001308.7, Office Action mailed Nov. 10, 2023", with machine translation, 4 pgs.

"German Application Serial No. 112022001308.7, Response filed Nov. 14, 2023 to Office Action mailed Nov. 10, 2023", with machine translation, 2 pgs.

"International Application Serial No. PCT/US2022/070864, International Preliminary Report on Patentability mailed Sep. 14, 2023", 13 pgs.

"International Application Serial No. PCT/US2022/070870, Article 19 Amendments filed Sep. 16, 2022", 15 pgs.

"International Application Serial No. PCT/US2022/070870, International Preliminary Report on Patentability mailed Sep. 14, 2023", 13 pgs.

"Japanese Application Serial No. 2023-553085, Notification of Reasons for Rejection mailed Sep. 2, 2024", W/English Translation, 8 pgs.

"Japanese Application Serial No. 2023-553085, Response filed Dec. 2, 2024 to Notification of Reasons for Rejection mailed Sep. 2, 2024", w/ English Claims, 14 pgs.

"Japanese Application Serial No. 2023-553086, Notification of Reasons for Refusal mailed Jul. 1, 2024", w/ English Translation, 14 pgs.

"Japanese Application Serial No. 2023-553086, Response filed Nov. 27, 2024 to Notification of Reasons for Refusal mailed Jul. 1, 2024", w/ English Claims, 19 pgs.

"U.S. Appl. No. 18/548,523, Restriction Requirement mailed Sep. 30, 2025", 9 pgs.

* cited by examiner

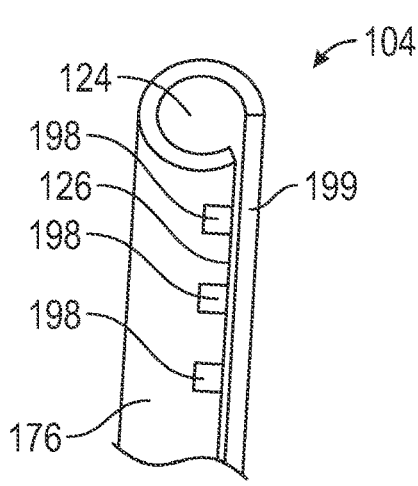
FIG. 13
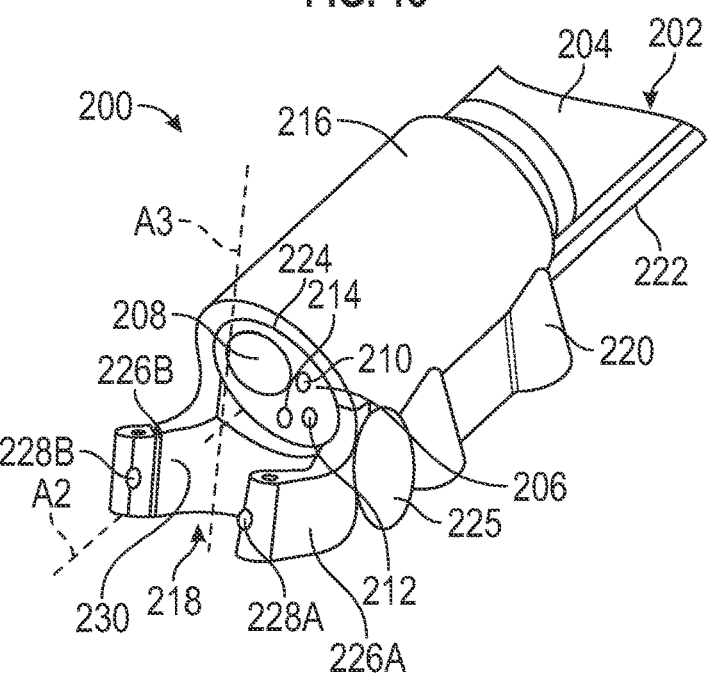
FIG. 14
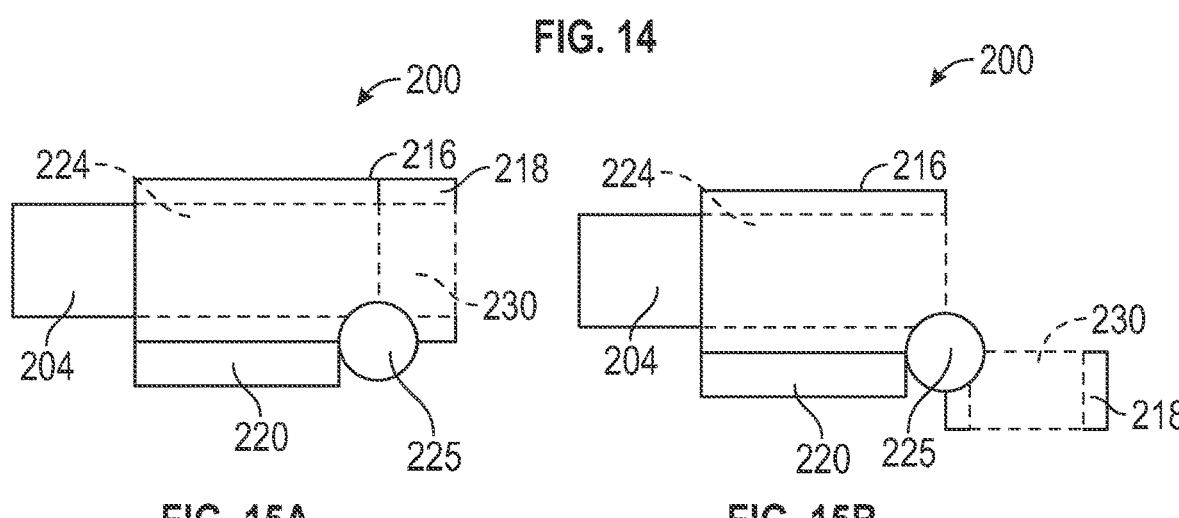
FIG. 15A                  FIG. 15B

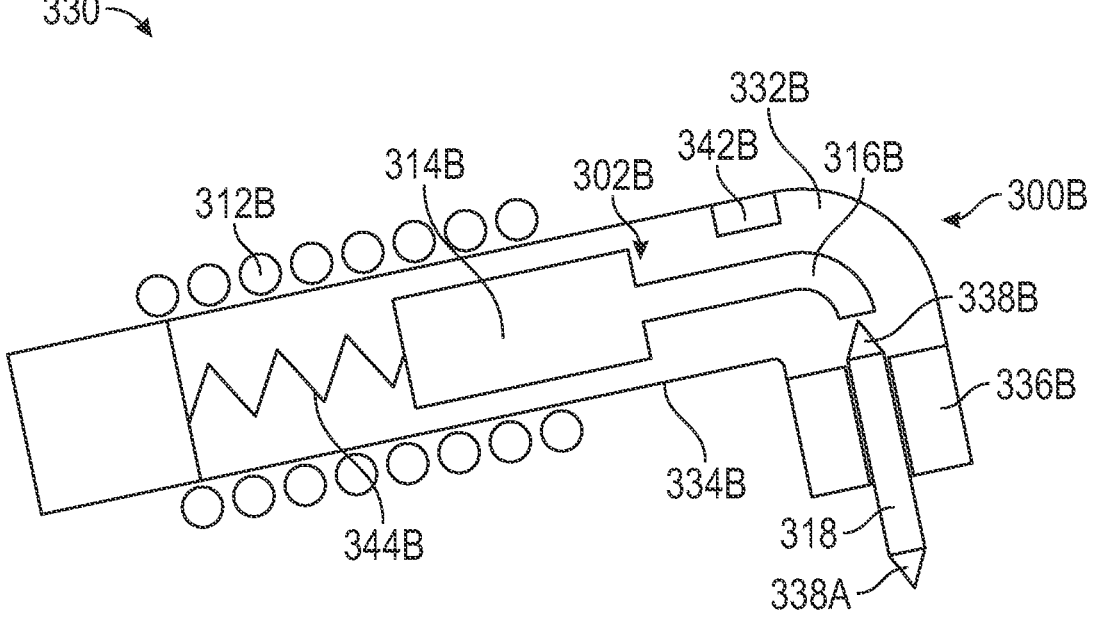
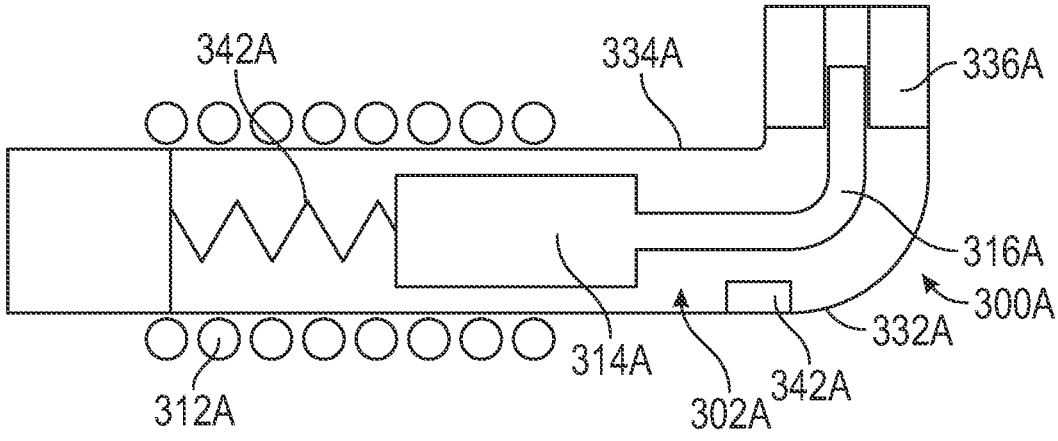
FIG. 22

ELECTRIC SUTURING DEVICES FOR ENDOSCOPY AND LAPAROSCOPY

CLAIM OF PRIORITY

This application is a U.S. National Stage filing under 35 U.S.C. § 371 from International Application No. PCT/US2022/070864, filed Feb. 28, 2022, which claims the benefit of priority to U.S. Provisional Patent Application Ser. No. 63/155,072, filed Mar. 1, 2021, and U.S. Provisional Patent Application Ser. No. 63/216,638, filed Jun. 30, 2021, which are hereby incorporated by reference herein in their entireties.

TECHNICAL FIELD

The present disclosure relates generally to medical devices comprising elongate bodies configured to be inserted into incisions or openings in anatomy of a patient to provide diagnostic or treatment operations.

More specifically, the present disclosure relates to medical devices, such as endoscopes, laparoscopes and other scopes, that can be inserted into anatomy of a patient, with or without the aid of another device, to facilitate performance of a medical procedure, such as by cutting, cauterizing or collecting tissue with a forceps.

BACKGROUND

Endoscopes can be used for one or more of 1) providing passage of other devices, e.g., therapeutic devices or tissue collection devices, toward various anatomical portions, and 2) imaging of such anatomical portions. Such anatomical portions can include gastrointestinal tract (e.g., esophagus, stomach, duodenum, pancreaticobiliary duct, intestines, colon, etc.), renal area (e.g., kidney(s), ureter, bladder, urethra, etc.), other internal organs (e.g., reproductive systems, sinus cavities, submucosal regions, respiratory tract), and the like.

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

In conventional endoscopy, the distal portion of the endoscope can be configured for supporting and orienting a therapeutic device, such as with the use of an elevator. In some systems, two endoscopes can be configured to work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

In view of the foregoing, medical procedures using scopes can involve time and skill to deliver the desired instrument to target anatomy where the instrument is to be used. Furthermore, many decisions must be made pre-operatively as to which instruments are to be used, how the scope is going to be delivered to the target anatomy, and which procedures will be performed on the target anatomy once it is delivered.

SUMMARY

The present inventors have recognized that problems to be solved with conventional medical devices, and in particular medical scopes, such as endoscopes and laparoscopes, used to treat and retrieve biological matter or perform other procedures, include, among other things, 1) the difficulty in navigating endoscopes, and instruments inserted therein, to locations within anatomical regions of a patient, 2) the difficulty of having to decide pre-operatively, before a scope is inserted into anatomy, which instruments are going to be used to perform the procedure without a) seeing the actual anatomy, b) knowing how the procedure actually progresses, and 3) the increased time and associated cost of having to remove and reinsert instruments into the anatomy to perform different procedures, such as tissue collection and suturing, particularly if the pre-operative decisions turn out to be ineffectual.

The present inventors have recognized that such problems can be particularly present in colonoscopy procedures, bariatric producers, and the like. In a colonoscopy procedure, a colonoscope is inserted into the patient to remove diseased tissue, such as polyps, from a colon. This typically involves removing mucosa from surfaces of the gastrointestinal tract. However, sometimes the tissue separation device, e.g., forceps, can puncture through a duct wall of the gastrointestinal tract. If the puncture is severe, it can be desirable to close the puncture, such as with suturing. However, suturing the puncture shut requires the introduction of a suturing device into the anatomy. Typical suturing devices involve dedicated suturing scopes or attachments that couple to the distal end of a scope. In the case of the latter, it can be undesirable to attach these devices before the endoscope is inserted into the anatomy because such devices can be cumbersome, can make the underlying procedure more difficult to perform, and likely will not be needed. As such, in either case, the endoscope must be withdrawn from the patient so that same instrument with the suturing attachment or another instrument can be inserted back into the patient to perform the suturing.

The present disclosure can help provide solutions to these and other problems by providing systems, devices and methods relating to endoscopy procedures to provide 1) a reinsertion sheath that can facilitate withdrawal of an endoscope from anatomy and reinsertion of the endoscope into the same anatomy without having to re-navigate the endoscope and 2) an attachable suturing device that can a) be simple to operate, b) be easily navigated when attached to a scope, c) minimize interference with performance of an underlying endoscope, and d) provide efficient and powerful suturing.

In an example, a method of withdrawing an endoscope from a target location in anatomy can comprise inserting the endoscope into an access portal in the anatomy to deliver a distal end portion of the endoscope to the target location, positioning a guide sheath around a proximal end portion of the endoscope, sliding the guide sheath along the endoscope to reach the distal end portion and withdrawing the endoscope from the guide sheath and anatomy.

In another example, a system for intraoperatively attaching a suturing device to an in situ endoscope can comprise an insertion sheath comprising an elongate tunnel body extending from a proximal end portion to a distal end portion and a slit extending axially along the elongate tunnel body, and a suturing device couplable in a releasable manner to an endoscope.

In an example, a re-insertion sheath for an endoscope can comprise an elongate body comprising a proximal end portion, a distal end portion and a skin extending axially between the proximal and distal end portions, and a slit extending along the shaft to allow circumferential expansion of the elongate body.

In another example, an electromagnetically driven suturing device can comprise a body, a first coil embedded in the body and a suturing element configured to be actuated by a magnetic field generated in the first coil.

In another example, an electro-magnetic suturing device can comprise a C-shaped housing comprising a first arm having a first end face, a first suturing track extending into the first end face, a second arm having a second end face at least partially opposing the first end face, a second suturing track extending into the second end face, a first coil embedded in the first arm, and a suturing element configured to be driven by a magnetic field generated by the first coil to move from the first suturing track to the second suturing track.

In an example, an electro-magnetic hammer suturing device can comprise a housing and a first coil embedded in the housing, a first shuttle configured to be reciprocated in the housing by an electromagnetic field generated by the first coil and suturing element configured to be actuated by the first shuttle.

BRIEF DESCRIPTION OF DRAWINGS

FIG. 13 is a schematic illustration of a reinsertion sheath comprising an elongate shaft comprising a lumen and a gap closeable by magnetic force.

FIG. 14 is a schematic perspective view of a suturing device attached to a distal end of an endoscope.

FIG. 15A is a side schematic view of the suturing device of FIG. 14 showing a suture body rotated flush with a coupler via a hinge.

FIG. 15B is a side schematic view of the suturing device of FIG. 15B showing the suture body rotated away from the coupler via the hinge.

FIG. 18 is a schematic cross-sectional view of a electro-magnetic suturing mechanism of the present disclosure comprising a magnetically-driven and spring-retracted suturing element.

FIG. 19 is a schematic cross-sectional view of a electro-magnetic suturing mechanism of the present disclosure comprising a magnetically-circulated suturing element.

FIG. 22 is a schematic cross-sectional view of the magnetically-driven hammer of FIG. 21 used with a suturing device having straight arms.

DETAILED DESCRIPTION

Figure 1:
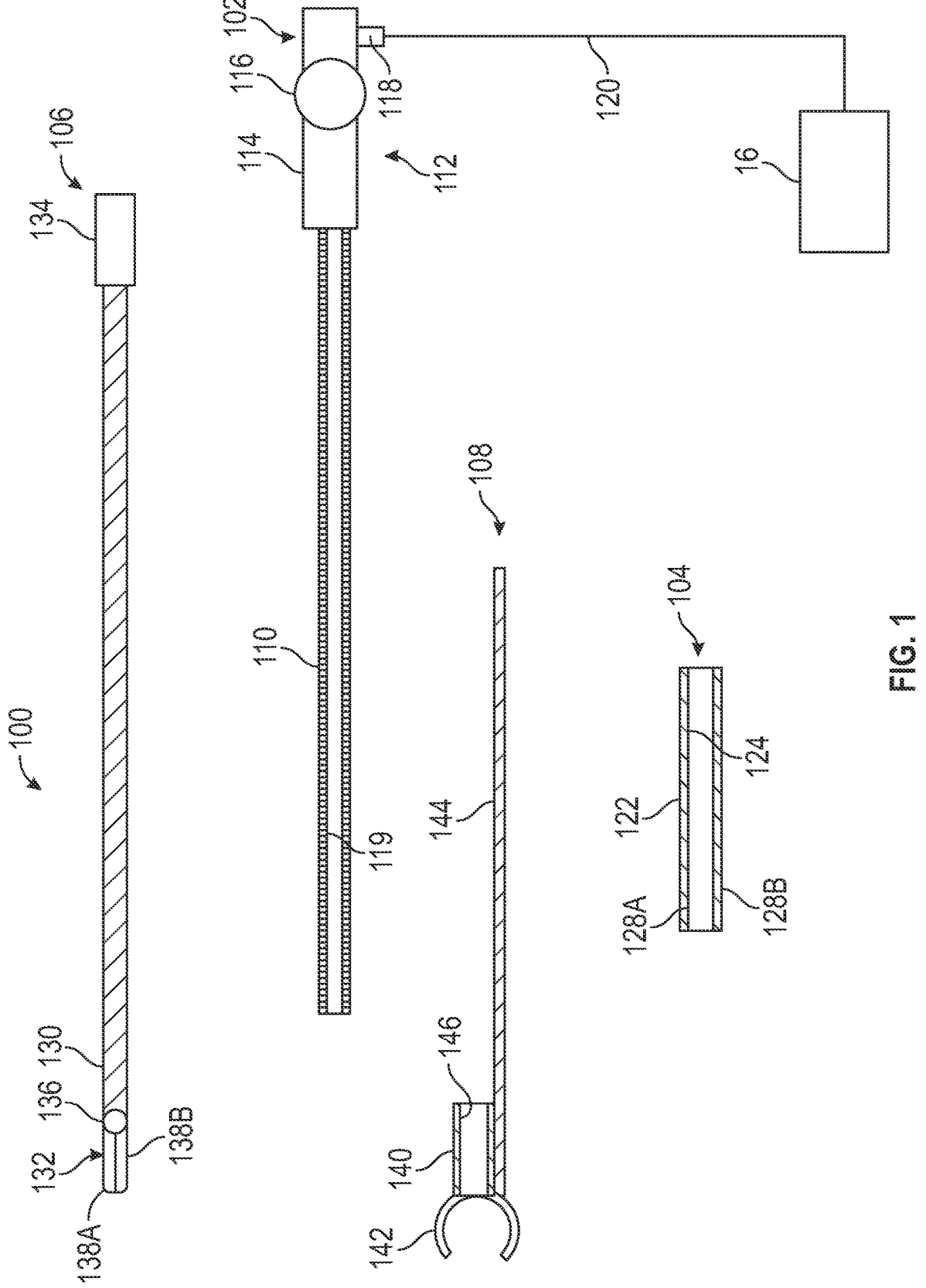
FIG. 1 is a schematic cross-sectional diagram of an endoscope system comprising a scope, a reinsertion sheath, a tissue separator device and a suturing attachment in an exploded configuration showing lumens through the system.
Figure 2:
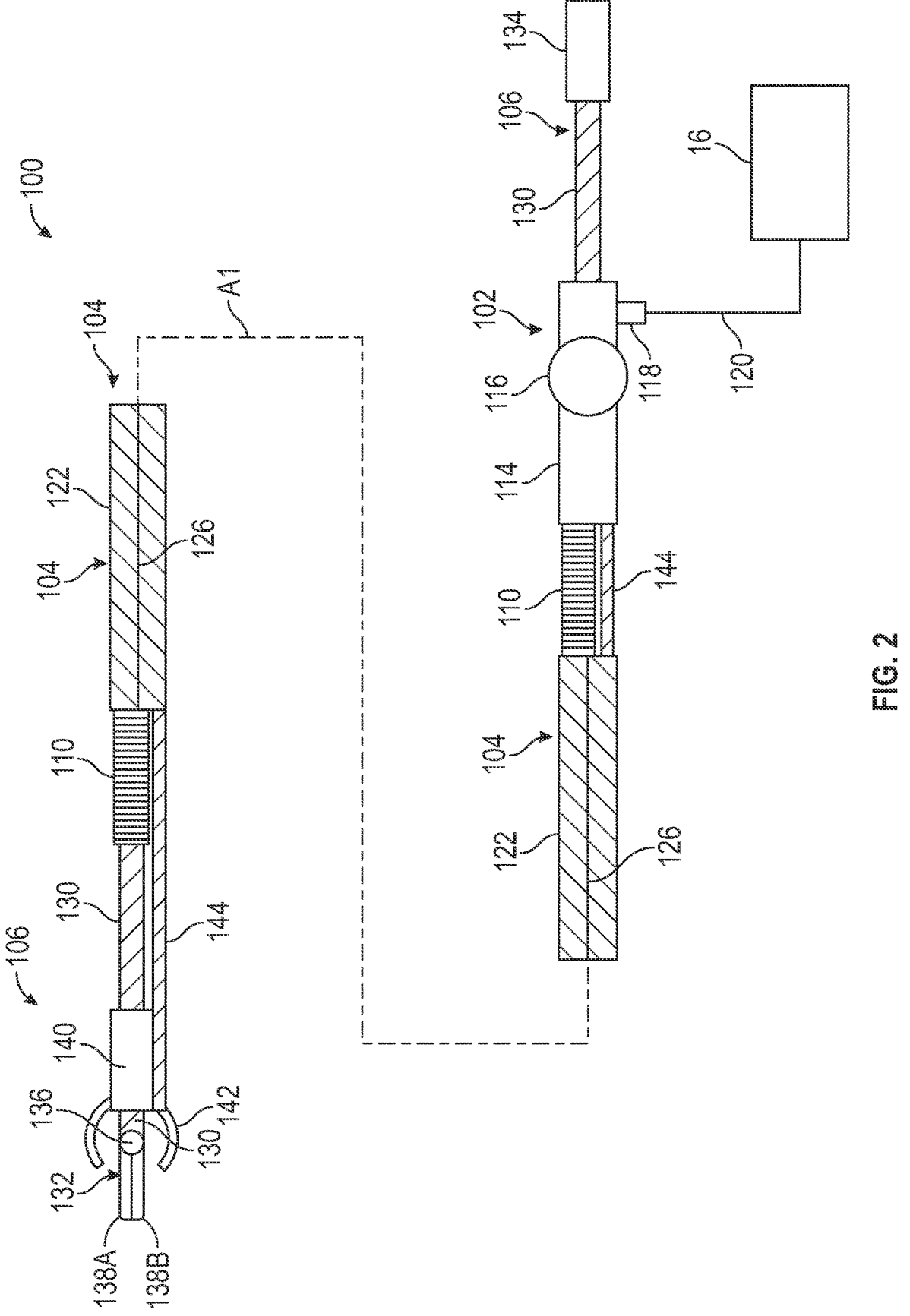
FIG. 2 is a schematic diagram of the endoscope system of FIG. 1 in an assembled state showing the tissue separator device and the suturing attachment positioned at a distal end of the scope, and the reinsertion sheath positioned around the scope.

FIG. 1 is a schematic diagram of endoscope system 100 in an exploded state. FIG. 2 is a schematic diagram of endoscope system 100 of FIG. 1 in an assembled state. FIGS. 1 and 2 are discussed concurrently. FIGS. 1 and 2 are not necessarily drawn to scale and may be exaggerated in certain aspects for illustrative purposes.

System 100 can comprise scope 102, reinsertion sheath 104, tissue separator device 106 and suture device 108. In FIG. 1, scope 102, reinsertion sheath 104, tissue separator device 106 and suturing attachment 108 are in a disassembled configuration. In FIG. 2, tissue separator device 106 and suturing attachment 108 are positioned at a distal end of scope 102, and reinsertion sheath 104 positioned around scope 102.

Scope 102, which is described in greater detail with reference to FIGS. 3-5B, can comprise elongate body 110 and controller 112, which can include grip 114, control knob 116 and coupler 118. Elongate body 110 can include lumen 119. Coupler 118 can connect to control unit 16 (FIG. 4) via cable 120.

Reinsertion sheath 104 can comprise shaft 122 and lumen 124. Shaft 122 can comprise slit 126 (FIG. 2) that forms flanges 128A and 128B.

Tissue separator device 106 can comprise shaft 130, tissue separator 132 and control device 134. Tissue separator 132 can comprise hinge 136 and separators 138A and 138B.

Suturing device 108 can comprise coupler 140, suturing body 142 and control element 144. Coupler 140 can comprise lumen 146.

FIG. 2 shows scope 102 nested inside of sheath 104, tissue separator device 106 nested inside scope 104, and suturing device 108 coupled to the end of scope 102. As such, as can be seen in FIG. 1, reinsertion sheath 104 can comprise lumen 124 and scope 102 can comprise lumen 119.

As is discussed in greater detail herein, endoscopy system 100 can be configured to provide the ability to insert scope 102 with tissue separator device 106 into anatomy and subsequently decide to assemble suturing device 108 to the distal end of scope 102. Reinsertion sheath 104 can be assembled to shaft 110 of scope 102 while shaft 110 is inserted into the anatomy. Reinsertion sheath 104 can include various features to facilitate assembly with the proximal end of shaft 110. For example, reinsertion sheath 104 can include slit 126 to allow shaft 122 to be slipped onto shaft 110 in a radial direction. Additionally, reinsertion sheath 104 can include axial contraction and expansion capabilities to facilitate the assembly and insertion steps. Thus, scope 102 can be withdrawn from reinsertion sheath 104, assembled with suturing device 108 and reinserted into reinsertion sheath 104, with or without tissue separator device 106.

Scope 102 can be configured as a fully functional endoscope including steerability, guidance capability, imaging capability, fluid dispensing and retrieving capabilities, and functional (e.g., therapeutic and diagnostic) capabilities, as well as a passageway for other instruments. Functionality of scope 102 is described in detail with reference to endoscope 14 of FIGS. 3-5B below and, as such, is only shown schematically in FIGS. 1 and 2.

The term "tissue separator device" is used throughout the present disclosure, however tissue separator device 106 can alternatively or additionally comprise a biological matter collection device, a biological matter retrieval device, a tissue collection device and tissue retrieval device. Tissue separator device 106 can be configured as any suitable device configured to obtain, retrieve, collect and/or remove tissue samples from within a patient. Tissue separator device 106 can comprise a component or device for interacting with a patient, such as those configured to cut, slice, pull, saw, punch, twist or auger tissue, and the like. Specifically, tissue separator device 106 can comprise any device suitable for removing tissue from a patient, such as a blade, punch or an auger. Tissue separator device 106 can be configured to physically separate portions of tissue of a patient from other larger portions of tissue in the patient. In additional examples, tissue separator device 106 can be configured to simply collect biological matter from the patient that does not need physical separation, such as mucus or fluid, that is already or naturally separate or distinct. In the illustrated example, tissue separator device 106 can comprise forceps having separators 138A and 138B configured as sharpened or serrated jaws pivotably connected at hinge 136. Tissue separator device 106 can, however, be configured as a variety of devices capable of collecting biological matter, such as a punch, an auger, a blade, a saw and the like, as mentioned. Tissue separator device 106 can be configured to hold a volume of collected biological matter, e.g., tissue, such as between separators 138A and 138B. As such, tissue separator device 106 can be configured to be withdrawn from scope 102 to obtain the collected biological matter, such as for diagnostic analysis or disposal.

Figure 3:
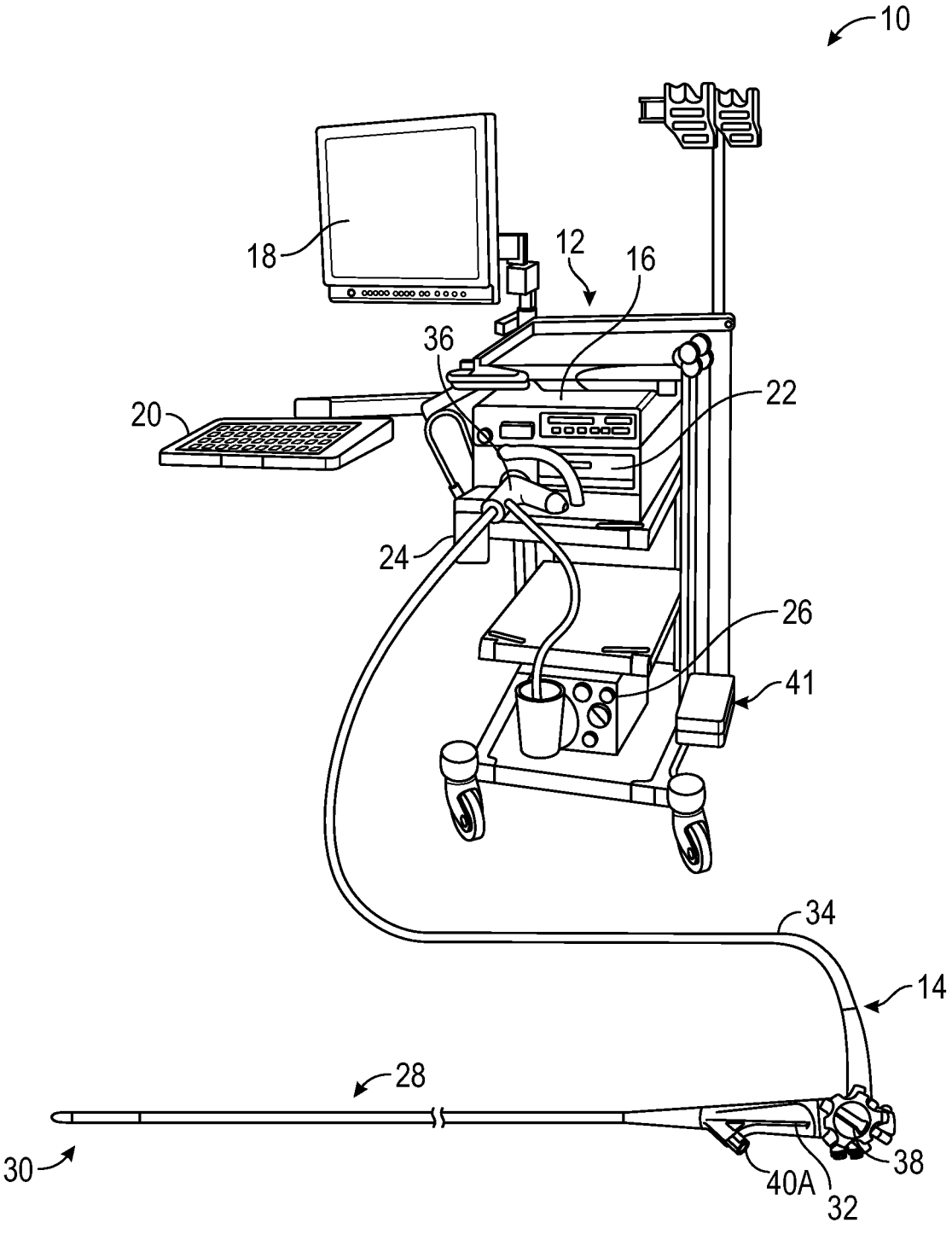
FIG. 3 is a schematic illustration of an imaging and control system comprising a control unit connected to the scope of FIGS. 1 and 2.

FIG. 3 is a schematic diagram of endoscopy system 10 comprising imaging and control system 12 and endoscope 14. The system of FIG. 3 is an illustrative example of an endoscopy system suitable for use with the systems, devices and methods described herein, such as colonoscopy procedures, bariatric producers, and the like, that can be used for removing and obtaining tissue or other biological matter from a patient for analysis or treatment of the patient. According to some examples, endoscope 14 can comprise scope 102 of FIGS. 1 and 2 and can be insertable into an anatomical region for imaging and/or to provide passage of one or more collection devices for biopsies, or one or more therapeutic devices for treatment of a disease state associated with the anatomical region. Endoscope 14 can, in advantageous aspects, interface with and connect to imaging and control system 12. In the illustrated example, endoscope 14 comprises an end-viewing colonoscope, though other types of endoscopes can be used with the features and teachings of the present disclosure.

Imaging and control system 12 can comprise control unit 16, output unit 18, input unit 20, light source unit 22, fluid source 24 and suction pump 26.

Imaging and control system 12 can include various ports for coupling with endoscopy system 10. For example, control unit 16 can include a data input/output port for receiving data from and communicating data to endoscope 14. Light source unit 22 can include an output port for transmitting light to endoscope 14, such as via a fiber optic link. Fluid source 24 can include a port for transmitting fluid to endoscope 14. Fluid source 24 can comprise a pump and a tank of fluid or can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator of endoscopy system 10 to control functions of endoscopy system 10 and view output of endoscope 14. Control unit 16 can additionally be used to generate signals or other outputs from treating the anatomical region into which endoscope 14 is inserted. In examples, control unit 16 can generate electrical output, acoustic output, a fluid output and the like for treating the anatomical region with, for example, cauterizing, cutting, freezing and the like.

Endoscope 14 can comprise insertion section 28, functional section 30 and handle section 32, which can be coupled to cable section 34 and coupler section 36. Coupler section 36 can be connected to control unit 16 to connect to endoscope 14 to multiple features of control unit 16, such as input unit 20, light source unit 22, fluid source 24 and suction pump 26.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by pull wires connected to control knob 38 on handle section 32) to maneuver the distal end through tortuous anatomical passageways (e.g., stomach, duodenum, kidney, ureter, colon, etc.). Insertion section 28 can also include one or more working channels (e.g., an internal lumen) that can be elongate and support insertion of one or more therapeutic tools of functional section 30, such as tissue separator device 106 of FIGS. 1 and 2. The working channel can extend between handle section 32 and functional section 30. Additional functionalities, such as fluid passages, guide wires, and pull wires can also be provided by insertion section 28 (e.g., via suction or irrigation passageways, and the like).

Handle section 32 can comprise knob 38 as well as port 40A. Knob 38 can be coupled to a pull wire, or other actuation mechanisms, extending through insertion section 28. Port 40A, as well as other ports, such as port 40B (FIG. 2), can be configured to couple various electrical cables, guide wires, auxiliary scopes, tissue collection devices, fluid tubes and the like to handle section 32 for coupling with insertion section 28. For example, tissue separator device 106 can be fed into endoscope 14 via port 40A.

Imaging and control system 12, according to examples, can be provided on a mobile platform (e.g., cart 41) with shelves for housing light source unit 22, suction pump 26, image processing unit 42 (FIG. 4), etc. Alternatively, several components of imaging and control system 12 shown in FIGS. 3 and 4 can be provided directly on endoscope 14 so as to make the endoscope "self-contained."

Functional section 30 can comprise components for treating and diagnosing anatomy of a patient. Functional section 30 can comprise an imaging device, an illumination device and an elevator. Functional section 30 can comprise imaging and illuminating components configured for end-viewing, e.g., viewing distally or axially beyond of functional section 30, such as is described further with reference to camera module 70 of FIGS. 5A and 5B.

Figure 4:
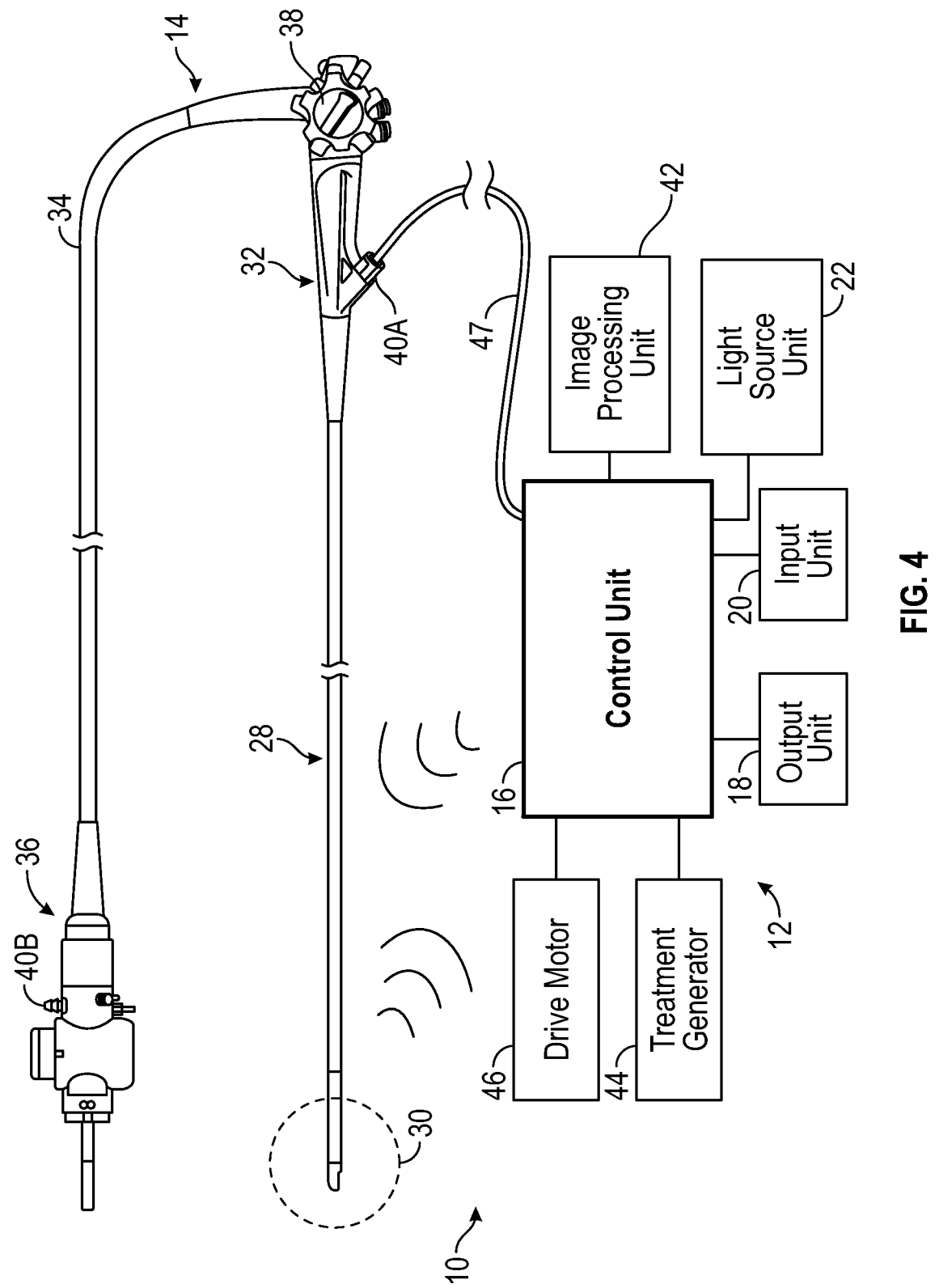
FIG. 4 is schematic diagram of the control unit of FIG. 3 connected to the scope.

FIG. 4 is a schematic diagram of endoscopy system 10 of FIG. 3 comprising imaging and control system 12 and endoscope 14. FIG. 4 schematically illustrates components of imaging and control system 12 coupled to endoscope 14, which in the illustrated example comprises an end-viewing colonoscope. Imaging and control system 12 can comprise control unit 16, which can include or be coupled to image processing unit 42, treatment generator 44 and drive unit 46, as well as light source unit 22, input unit 20 and output unit 18. Coupler section 36 can be connected to control unit 16 to connect to endoscope 14 to multiple features of control unit 16, such as image processing unit 42 and treatment generator 44. In examples, port 40A can be used to insert another instrument or device, such as a daughter scope or auxiliary scope, into endoscope 14. Such instruments and devices can be independently connected to control unit 16 via cable 47. In examples, port 40B can be used to connect coupler section 36 to various inputs and outputs, such as video, air, light and electric.

Image processing unit 42 and light source unit 22 can each interface with endoscope 14 (e.g., at functional section 30) by wired or wireless electrical connections. Imaging and control system 12 can accordingly illuminate an anatomical region, collect signals representing the anatomical region, process signals representing the anatomical region, and display images representing the anatomical region on output unit 18, which can comprise a cathode ray tube, an LCD display, an LED display and other graphical user interfaces.

Imaging and control system 12 can include light source unit 22 to illuminate the anatomical region using light of desired spectrum (e.g., broadband white light, narrow-band imaging using preferred electromagnetic wavelengths, and the like). Imaging and control system 12 can connect (e.g., via an endoscope connector) to endoscope 14 for signal transmission (e.g., light output from light source, video signals from imaging system in the distal end, diagnostic and sensor signals from a diagnostic device, and the like).

Fluid source 24 (FIG. 1) can be in communication with control unit 16 and can comprise one or more sources of air, saline or other fluids, as well as associated fluid pathways (e.g., air channels, irrigation channels, suction channels) and connectors (barb fittings, fluid seals, valves and the like). Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 5B:
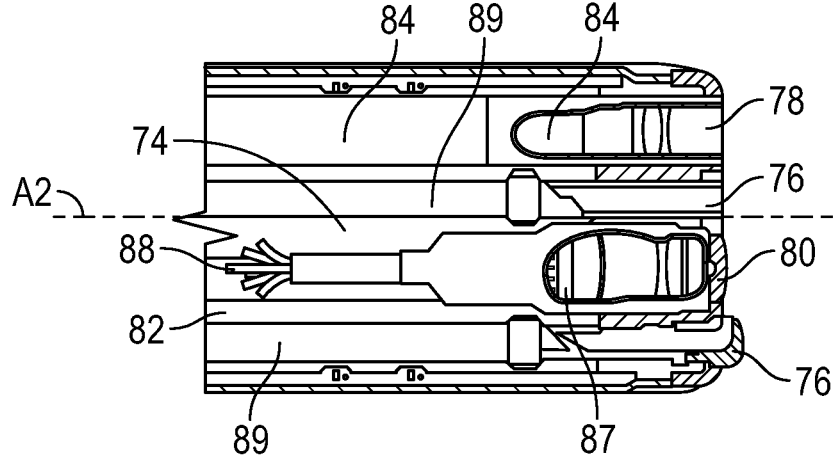
FIG. 5B is a cross-sectional view taken along section 5B-5B of FIG. 5A showing components of the camera module.
Figure 5A:
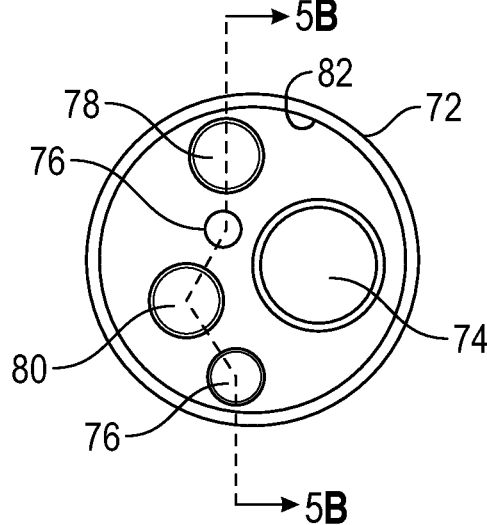
FIG. 5A is an end view of a camera module including optical and functional components suitable for use with the scope of FIGS. 1-4.

FIGS. 5A and 5B illustrate an example of functional section 30 of cholangioscope 14 of FIG. 4. FIG. 5A illustrates an end view of functional section 30 and FIG. 5B illustrates a cross-sectional view of functional section 30 taken along section plane 5B-5B of FIG. 5A. FIGS. 5A and 5B each illustrate "end-viewing endoscope" (e.g., gastroscope, colonoscope, cholangioscope, etc.) camera module 70. In end-viewing endoscope camera module 70, illumination and imaging systems are positioned such that the viewing angle of the imaging system corresponds to a target anatomy located adjacent (e.g., distal of) an end of endoscope 14 and in line with central longitudinal axis A1 of endoscope 14.

In the example of FIGS. 5A and 5B, end-viewing endoscope camera module 70 can comprise housing 72, therapy unit 74, fluid outlets 76, illumination lens 78 and objective lens 80. Housing 72 can comprise and endcap for insertion section 28, thereby providing a seal to lumen 82.

As can be seen in FIG. 5B, insertion section 28 can comprise lumen 82 through which various components can be extended to connect functional section 30 with handle section 32 (FIG. 4). For example, illumination lens 78 can be connected to light transmitter 84, which can comprise a fiber optic cable or cable bundle extending to light source unit 22 (FIG. 4). Likewise, objective lens 80 can be coupled to imaging unit 87, which can be coupled to wiring 88. Also, fluid outlets 76 can be coupled to fluid lines 89, which can comprise a tube extending to fluid source 24 (FIG. 4). In examples, one of fluid outlets 76 can comprise an inlet connected to a fluid line 89 configured for suction, such as being connected to a vacuum, for recovery of lavage and irrigation fluid. Other elongate elements, e.g., tubes, wires, cables, can extend through lumen 82 to connect functional section 30 with components of endoscopy system 10, such as suction pump 26 (FIG. 4) and treatment generator 44 (FIG. 4). For example, therapy unit 74 can comprise a wide-diameter lumen for receiving other treatment components, such as cutting devices and therapeutic devices including tissue separator device 106.

Endoscope camera module 70 can also include a photosensitive element, such as a charge-coupled device ("CCD" sensor) or a complementary metal-oxide semiconductor ("CMOS") sensor. In either example, imaging unit 87 can be coupled (e.g., via wired or wireless connections) to image processing unit 42 (FIG. 4) to transmit signals from the photosensitive element representing images (e.g., video signals) to image processing unit 42, in turn to be displayed on a display such as output unit 18. In various examples, imaging and control system 12 and imaging unit 87 can be configured to provide outputs at desired resolution (e.g., at least 480p, at least 720p, at least 1080p, at least 4K UHD, etc.) suitable for endoscopy procedures.

As described herein, working channel 74 can be used to deliver tissue separator device 106 to target tissue. Additionally, suturing device 108 can be positioned over the distal end portion of housing 72 to provide suturing functionality distal of illumination lens 78 and objective lens 80. Furthermore, reinsertion sheath 104 can be positioned around insertion section 28 proximal of housing 72 to allow endoscope 14 to be inserted into and withdrawn from anatomy without any or with minimal steering and navigation.

Figures 6, 7, 8A, 8B:
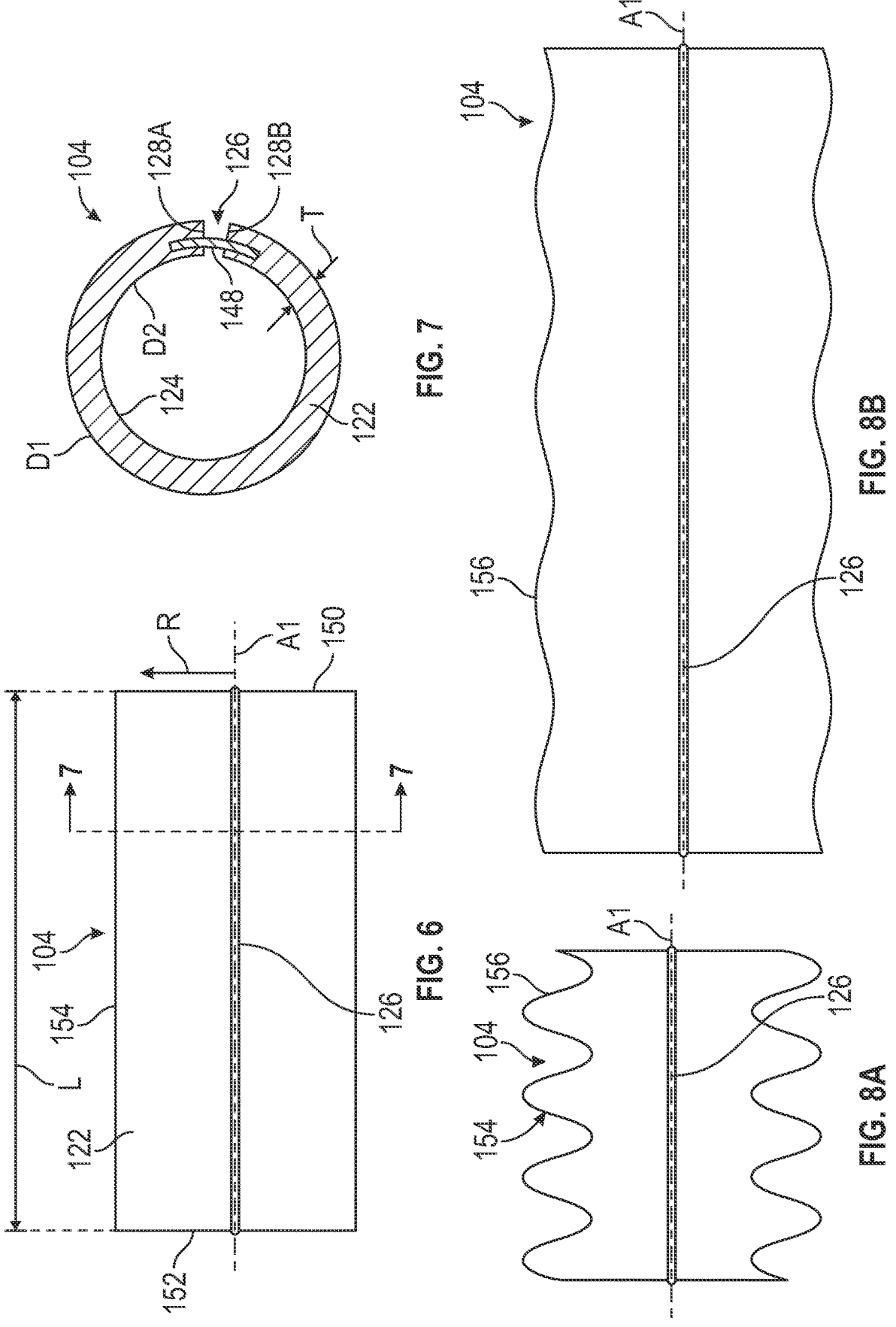
FIG. 6 is a schematic side view of a reinsertion sheath of the present disclosure showing a slit in skin of a shaft.
FIG. 7 is a schematic cross-sectional view taken along section 7-7 of FIG. 6 showing an internal lumen of the reinsertion sheath.
FIG. 8A is schematic side view of the reinsertion sheath of FIG. 6 in a compressed state such that the skin is corrugated.
FIG. 8B is a schematic side view of the reinsertion sheath of FIG. 8A in an extended state such that the skin is expanded.

FIG. 6 is a schematic side view of reinsertion sheath 104 of the present disclosure showing slit 126 in shaft 122. FIG. 7 is a schematic cross-sectional view of reinsertion sheath 104 of FIG. 6 showing internal lumen 124 extending within shaft 122. Shaft 122 can include slit 126 that forms flanges 128A and 128B. In examples, shaft 122 can further comprise rotating door 148. FIGS. 6 and 7 are discussed concurrently.

Shaft 122 can extend axially from first, proximal end 150 to second, distal end 152 along axis A. In the illustrated example, flanges 128A and 128B can form end faces that are separated by a distance. In other examples, flanges 128A and 128B can contact each other to form a continuous three-hundred-sixty-degree perimeter. In examples, rotatable door 148 can extend from a channel in on of flanges 128A into a channel in another of flanges 128B. Rotatable door 148 can be opened to allow for a scope to be positioned inside lumen 124 and then can be rotated closed to secure the scope therein.

Lumen 124 can extend between proximal end 150 and distal end 152. Lumen 124 can extend from axis A1 in radial direction R. Walls of shaft 122 can have thickness T. The outer diameter D1 of shaft 122 can be configured to fit into a desired anatomy. Inner diameter D2 of shaft 122 can be sized to fit around shaft 110 of scope 120 (FIGS. 1 and 2). Shaft 122 is illustrated as having length L, which, as shown in FIGS. 8A and 8B, can be compacted and expanded as desired in various examples. Shaft 122 is not drawn to scale in FIG. 6 and thus can be longer in direction L than illustrated.

Shaft 122 can be fabricated from any suitable biocompatible material. In examples, shaft 122 can be made of a polymer material. The material of shaft 122 can allow for reinsertion sheath 104 to be deformed via manipulation by an operator, such as a surgeon. For example, an operator of insertion sheath 104 can pull flanges 128A and 128B apart to allow scope 102 (FIG. 1) to be positioned inside lumen 124. However, when deployed in anatomy, reinsertion sheath 104 can be configured to retain rigidity to displace anatomy and guide an instrument through lumen 124. Thickness T can be selected to allow shaft 104 to be contracted or crumpled, as shown in FIG. 8A, but extended to provide the desired passageway through anatomy. Thus, thickness T can be selected to allow an operator to manually contract or extend length L, but once extended shaft 122 can be configured to maintain shape.

FIG. 6 is intended to illustrate the fully extended length of shaft 122 at rest when not subject to any compressive or tensile loading such that the outer surface 154 is approximately straight. However, shaft 122 can be subject to compressive forces to reduce length L, as shown in FIG. 8A.

FIG. 8A is schematic side view of reinsertion sheath 104 of FIGS. 6 and 7 in a compressed state. Reinsertion sheath 104 can be compressed along axis A1 to the corrugated state of FIG. 8A. Outer surface 154 of reinsertion sheath 104 can be become compressed to form undulations 156 as the material of shaft 122 becomes furrowed.

FIG. 8B is a schematic side view of reinsertion sheath 104 of FIG. 8A in an extended state along axis A1. As such, undulations 156 can become muted as shaft 122 becomes furrowed. In examples, reinsertion sheath 104 can be fabricated from a rigid corrugated plastic having radially extending rigid portions connected by living hinges such that the reinsertion sheath can be selectively extended and bent is desired orientations.

In examples, the material of shaft 122 can be compliant to allow sheath 104 to be expanded and contracted in the radial direction along axis A1. The material of shaft 122 can comprise a flexible polymeric sheet reinforced with webbing, such as a ripstop material. In order to provide radial stiffness to sheath 104, shaft 122 can be provided with various stiffening means to retain the desired outer diameter of sheath 104, as discussed with reference to FIGS. 9A-10B.

Figures 9A, 9B, 10A, 10B:
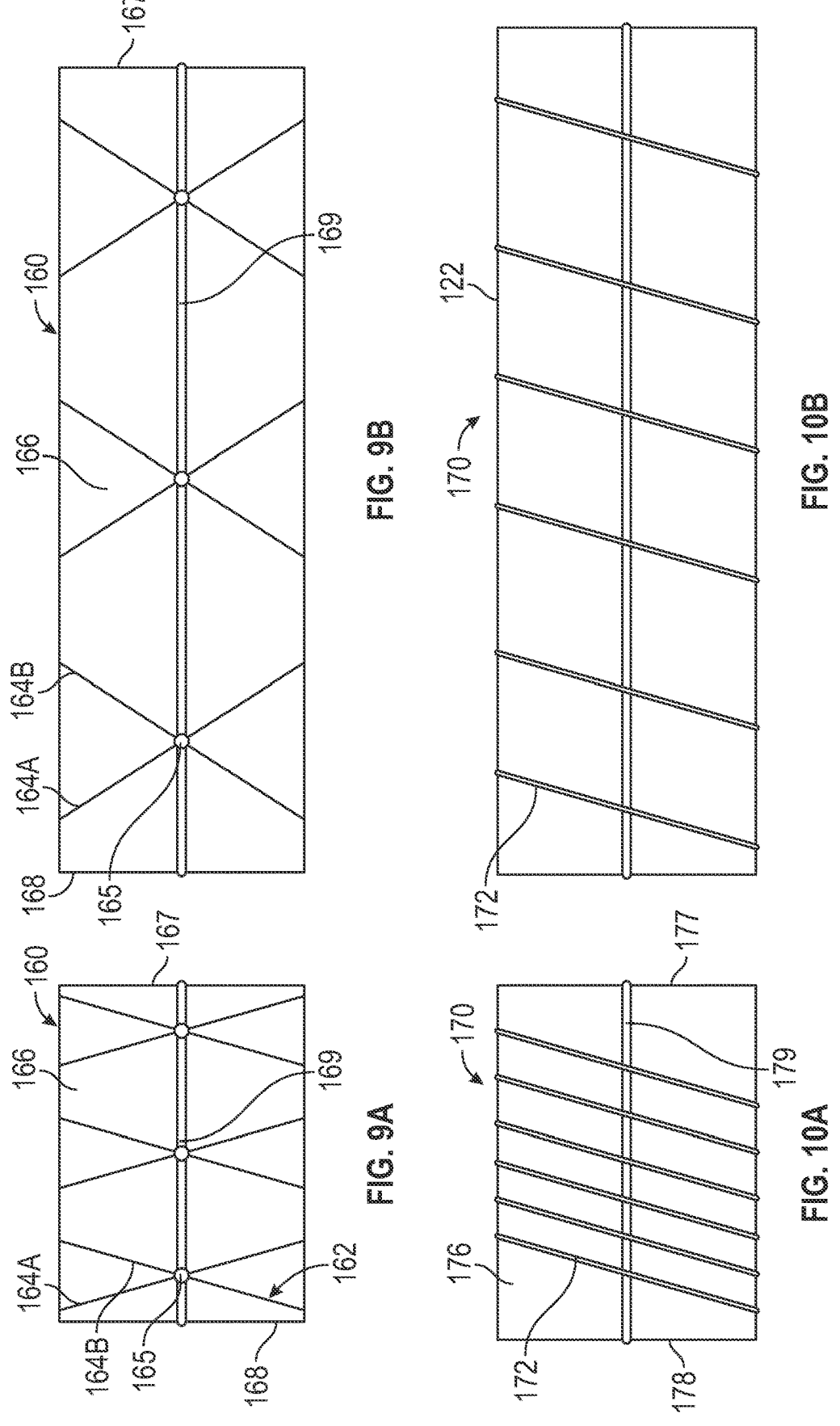
FIG. 9A is a schematic side view of the reinsertion sheath of FIG. 6 having expandable supports in a compressed state.
FIG. 9B is a schematic side view of the reinsertion sheath of FIG. 9A in an extended state.
FIG. 10A is a schematic side view of the reinsertion sheath of FIG. 6 having a helical support member in a compressed state.
FIG. 10B is a schematic side view of the reinsertion sheath of FIG. 10A in an extended state.

FIG. 9A is a schematic side view of reinsertion sheath 160 having expandable supports 162 in a contracted state. FIG. 9B is a schematic side view of reinsertion sheath 160 of FIG. 9A in an extended state. FIGS. 9A and 9B are discussed concurrently.

Reinsertion sheath 160 can be constructed similarly to reinsertion sheath 104 of FIGS. 6-8B with the addition of cross-supports or struts 164A and 164B. Reinsertion sheath 160 can comprise expandable supports 162 attached to body 166, which can extend from first end 167 to second end 168. Expandable supports 162 can comprise struts 164A and 164B that can be connected at hinges 165. Slit 169 can extend across body 166. Slit 169 is schematically illustrated as extending along body 166. Slit 169 can be positioned on body 166 on an opposite side as expandable supports 162. As such, when viewed from an end of reinsertion sheath 160, such as the view of FIG. 7, struts 164A and 164B can have a C-shape with slit 169 forming the ends of the C.

Struts 164A and 164B can comprise wires or bars embedded in or attached to the material of body 166 inside or outside of lumen 124. Struts 164A and 164B can comprise rigid or stiff members to support the material of body 166 in the radial and circumferential directions relative to axis A1. Hinges 165 can comprise pivot points to allow struts 164A and 164B to rotate relative to each other while maintaining contact to provide radial and circumferential support to body 166. Struts 164A and 164B can be configured to minimally impact the axial rigidity of reinsertion sheath 160.

Body 166 can provide a skin over expandable supports 162 to provide a shaft structure. The skin can comprise a flexible polymeric sheet reinforced with webbing, such as a ripstop material. Body 166 can be configured to provide the desired axial stiffness to reinsertion sheath 160.

FIG. 9A shows struts 164A and 164B in a collapsed state where ends of struts 164A and 164B are closer together. However, as can be seen in FIG. 9B, struts 164A and 164B can be opened by rotation at hinges 165 as reinsertion sheath 160 is expanded such that ends 167 and 168 are further apart as compared to FIG. 9A.

Thus, body 166 of reinsertion sheath 160 can be compressed with struts 164A and 164B rotated at hinges 165 to the state of FIG. 9A to facilitate assembly with a scope. When it is desired that reinsertion sheath 160 be deployed, an operator can pull body 166 apart in the circumferential direction at slit 169 to allow sheath 160 to be positioned over shaft 110 of scope 102. In particular, collapsed reinsertion sheath 160 can be positioned over a proximal end of shaft 110 while a distal end of shaft 110 is positioned in anatomy of a patient. Once positioned over shaft 110, an operator can push the distal end of reinsertion sheath 160 along shaft 110 into anatomy of the patient. As mentioned, the stiffness of body 166 can be such that the operator can unfurrow body 166 from the collapsed configuration, but as body 166 is incrementally increased in size, body 166 can maintain its own shape under pressure from the anatomy. Struts 164A and 164B can provide radial stiffening to reinsertion sheath 160 to allow body 166 to resist the anatomy and allow other devices and instruments to be inserted therein, such as scope 102 (FIGS. 1 and 2). Thus, the length L (FIG. 6) of reinsertion sheath 160 can be long enough to reach the distal end of scope 102 or close thereto. Once reinsertion sheath 160 is deployed into the anatomy and fully extended or sufficiently extended to reach an end portion of scope 102, scope 102 can be withdrawn and reinsertion sheath 160 can remain. Inner diameter D2 (FIG. 7) can thus provide a body forming a tunnel to the desired anatomy. As such, scope 102 need not be independently navigated back to the anatomy, but can be simply inserted into reinsertion sheath 160 to reach the desired anatomy. Thus, scope 102 can be withdrawn from anatomy through reinsertion sheath 160 to attach one of the suturing devices described herein with reference to FIGS. 14-23 and then reinserted with the suturing device to reach the same anatomy.

FIG. 10A is a schematic side view of reinsertion sheath 170 having helical support member 172 in a contracted state. FIG. 10B is a schematic side view of reinsertion sheath 170 of FIG. 10A in an extended state. FIGS. 10A and 10B are discussed concurrently.

Reinsertion sheath 170 can comprise body 176 extending between ends 177 and 178. Slit 179 can extend along body 176. Reinsertion sheath 170 can be constructed similarly to reinsertion sheath 160 of FIGS. 9A and 9B with expandable supports 162 being replaced with helical support member 172. Helical support member 172 can comprise a rigid or stiff member that spirals along reinsertion sheath 170 between ends 177 and 178.

Slit 179 can extend across body 176. Slit 179 is schematically illustrated as extending along body 176. Slit 179 can be positioned on body 176 on an opposite side as helical support member 172. As such, when viewed from an end of reinsertion sheath 170, such as the view of FIG. 7, helical support member 172 can have a C-shape with slit 169 forming the ends of the C. As such, helical support member 172 may not form a continuous helical shape between ends 177 and 178, but can be formed of a plurality of helical segments.

As with expandable supports 162 of FIGS. 9A and 9B, helical support member 172 can provide radial and circumferential stiffening to body 176 to allow for support against the pressures of anatomy and to form a body defining a tunnel for the insertion of instruments. Helical support member 172 can, however, allow for axial expansion and contraction of body 176 such that the native stiffness of body 176 can be utilized to allow for axial contraction and expansion of reinsertion sheath 170 to allow for deployment as is described with reference to FIGS. 9A and 9B.

Figures 11, 12A, 12B:
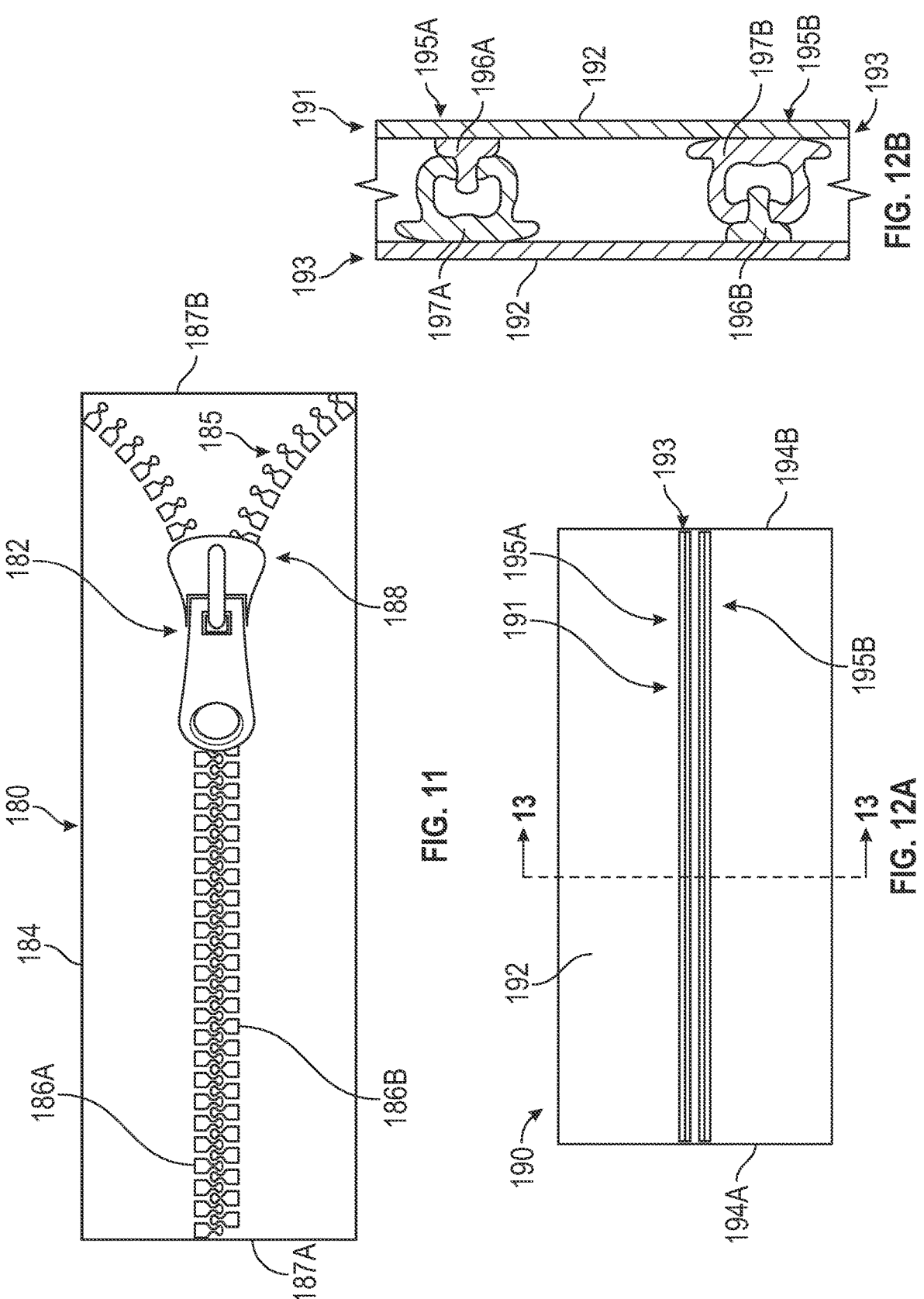
FIG. 11 is a schematic side view of a segment of a reinsertion sheath of the present disclosure having a zipper closure mechanism.
FIG. 12A is a schematic side view of a segment of a reinsertion sheath of the present disclosure having an interlocking rail closure mechanism.
FIG. 12B is a cross-sectional view taken along section 12B-12B of FIG. 12A showing rails of the interlocking rail closure mechanism.

FIG. 11 is a schematic side view of a segment of reinsertion sheath 180 of the present disclosure having zipper closure mechanism 182. Sheath 180 can comprise shaft 184 and slit 185. Shaft can extend from first side 187A to second side 187B. Zipper closure mechanism 182 can comprise opposing teeth 186A and 186B on opposite sides of slit 185 and shuttle 188. Zipper closure mechanism 182 is not necessarily drawn to scale in FIG. 11. Reinsertion sheath 180 of FIG. 11 can be used in conjunction with any reinsertion sheath described herein, such as reinsertion sheaths 104, 160 and 170. Zipper closure mechanism 182 can be configured to extend along any of slits 126, 169 and 179.

Teeth 186A can be positioned along one side of slit 185. Teeth 186B can be positioned along a second side of slit 185. Teeth 186A and 186B can be staggered so that teeth 186B can fit between teeth 186B and vice versa. Shuttle 188 can be used to couple and uncouple teeth 186A and 186B. As such, zipper closure mechanism 182 can function as a zipper in a conventional manner.

Zipper closure mechanism 182 can be released to allow teeth 186A and 186B to separate. As such, reinsertion sheath 180 can be positioned around a shaft of a scope. Reinsertion sheath 180 can be inserted into anatomy with first end 187A positioned distally to enter the anatomy first. As shaft 184 is pushed or fed distally into the anatomy, shuttle 188 can be pulled proximally to bring teeth 186A and 186B into engagement. Thus, as shaft 184 is unfurled and fed further into anatomy, shuttle 180 can be advanced to close-up shaft 184.

FIG. 12A is a schematic side view of a segment of reinsertion sheath 190 of the present disclosure having interlocking rail closure mechanism 191. Reinsertion sheath 190 can comprise shaft 192 and slit 193. Shaft 192 can extend from first end 194A to second end 194B. Interlocking rail closure mechanism 191 can comprise first rail 195A and second rail 195B. Interlocking rail closure mechanism 191 is not necessarily drawn to scale in FIG. 12A. Reinsertion sheath 190 of FIG. 12A can be used in conjunction with any reinsertion sheath described herein, such as reinsertion sheaths 104, 160 and 170 described herein. Interlocking rail closure mechanism 191 can be configured to extend along any of slits 126, 169 and 179.

First rail 195A and second rail 195B can be placed on ends of shaft 192 forming slit 193 in an overlapping manner, as is described with reference to FIG. 13.

FIG. 12B is a cross-sectional view of reinsertion sheath closure mechanism 191 of FIG. 12A. Interlocking rail closure mechanism 191 can comprise first rail 195A and second rail 195B. First rail 195A can comprise first projection 196A and first slot 197A. Second rail 195B can comprise second projection 196B and second slot 197B. Projections 196A and 196B can comprise bulbous heads and each rail of slots 197A and 197B can comprise inwardly oriented teeth configured to engage with the bulbous heads. In an example, interlocking rail closure mechanism 191 can be constructed according to U.S. Pat. No. 7,137,736 to Pawloski et al., which is hereby incorporated by reference in its entirety.

As shown in FIG. 12B, ends of slit 193 can be pulled so that portions of shaft 192 overlap to allow slots 197A and 197B and projections 196A and 196B to interface, respectively. Projection 196A and slot 197A can be placed in an overlapping arrangement and pressed together by an operator to lock. Likewise, projection 196B and slot 197B can be placed in an overlapping arrangement and pressed together by an operator to lock. In an example, a shuttle can be provided on interlocking rail closure mechanism 191 to facilitate pushing of projections 196A and 196B together with slots 197A and 197B and separation of said components. Either of ends 194A and 194B can be fed into anatomy first.

FIG. 13 is a schematic illustration of reinsertion sheath 104 comprising elongate shaft 176 comprising lumen 124 and gap 126. Gap 126 can include a plurality of magnetic members 198 and metallic strip 199. Magnetic members 198 can be attracted to metallic strip 199 via magnetic forces. Thus, at rest, magnetic members 198 can pull ends of elongate shaft 176 along gap 126 closed. However, magnetic members 198 can be pushed away from metallic strip 199 to allow the device or object to enter lumen 124 in the radial direction. After the device or object enters lumen 124, magnetic members 198 can be pulled back into engagement with metallic strip 199 via magnetic attraction. As such, sheath 104 can be easily slipped over elongate body 110 of scope 102 while scope 102 is inserted into anatomy.

FIGS. 6-13 illustrate examples of reinsertion sheaths of the present disclosure having various features that can be used together or separately or in various combinations thereof. Reinsertion sheaths of the present disclosure can provide a body that forms a tunnel through anatomy that can guide another instrument inserted therein to a desired location. The reinsertion sheaths can be positioned within anatomy using another instrument previously navigated (e.g., steered, turned, controlled and manipulated to be pushed through desired anatomical features and ducts) to a target tissue site in the anatomy. The previously inserted instrument can thus serve as a type of guide feature similar to a guide wire to direct reinsertion sheath to the target tissue site without having to actively navigate the reinsertion sheath or with minimal manipulation or cajoling. As discussed herein, the reinsertion sheaths can be circumferentially openable to allow positioning of the reinsertion sheath over an instrument in a radial direction relative to an axis of the instrument. Thus, the reinsertion sheaths can be positioned over a proximal end of the instrument while a distal end is positioned within anatomy. Material of the reinsertion sheaths can form skins radially reinforced with wires or bars and that can be axially compacted, e.g., contracted or furled, in an axial direction so as to fit over only a portion of the length of the instrument, e.g., a portion of the instrument not inserted into anatomy. As such, the reinsertion sheath can be more easily manipulated. Once positioned over the proximal portion of the inserted instrument, the reinsertion sheath can be expanded or unfurled to push a distal portion of the insertion sheath into anatomy of the patient around the instrument. Axially collapsible support features can be used to provide the reinsertion sheaths with radial rigidity to push anatomy away from the center axis of the reinsertion sheath. Thus, once the guide instrument is removed from the reinsertion sheath, an open tunnel can be provided within reinsertion sheath to provide a direct route to the target tissue site.

FIG. 14 is a schematic perspective view of suturing device 200 attached to endoscope 202. Endoscope 202 can be constructed according to any of the scopes described herein and can comprise shaft 204, end face 206, working channel 208, imaging component 210, illumination component 212 and irrigation channel 214. Suturing device 200 can comprise coupler 216, suture body 218, housing 220, control element 222 and hinge 225. As discussed herein, suture body 218 can comprise devices for driving a suturing element, such as a needle, staple, shuttle and the like, to pull and/or push suturing material through tissue. In examples, an electro-magnetic driving device can be used to move an arcuate suturing needle via direct or indirect electro-magnetic force. Although suturing device 200 is described as being a separately attachable device to scope 202, in additional examples, suturing device 200 or components thereof (e.g., suture body 218, housing 220, control element 222 and hinge 225) can be integrated directly into scope 202.

Coupler 216 can comprise a rigid or compliant body that facilitates coupling with shaft 204. Coupler 216 can comprise an annular body having channel 224 passing through from one end to the other end along axis A2. Shaft 204 can extend along axis A1 of previous figures. Shaft 204 of endoscope 202 can be sized to fit into channel 224 in a concentric manner to retain suturing device 200 attached to endoscope 202. In examples, an interference fit can be formed between channel 224 and shaft 204. Channel 224 can extend straight to the distal end of coupler 216 or can include a flange to prevent coupler 216 from being pushed proximally along shaft 204. Such a flange can ensure proper positioning of suture body 218 relative to end face 206 to ensure suture body 218 is within the field of view of imaging component 210 and illumination component 212. However, channel 224 can allow enough of end face 206 to be exposed to not interfere with working channel 208, imaging component 210, illumination component 212 and irrigation channel 214. Coupler 216 can, therefore, form a cap that can be releasably attached to shaft 204. Channel 224 and shaft 204 can additionally include features (not visible in FIG. 14) to facilitate rotational alignment between suturing device 200 and scope 202, such as to provide proper orientation between working channel 208, imaging component 210, illumination component 212 and irrigation channel 214 of scope 202 and socket 230 of suturing device 200. In examples, the rotational alignment features can comprise an axially extending channel extending into end face 206 at a particular circumferential location that can receive a corresponding axially extending flange on channel 224, or the reverse configuration.

Suture body 218 can extend distally of coupler 216 so as to be positioned distally and in view of imaging component 210 and illumination component 212. Suture body 218 can be connected to coupler 216 via hinge 225. Suture body 218 can include opposing arms 226A and 226B that include suture tracks 228A and 228B, respectively. Opposing arms 226A and 226B can be positioned around socket 230, which can form a space for receiving tissue for suturing. Suture tracks 228A and 228B can extend in an arcuate manner into end faces 229A and 229B, respectively, and can have a radius of curvature centered around axis A3. Control element 222 can extend from suture body 218 and can comprise a cable or wire configured to provide power and control signals to components within suture body 218, such as electro-magnetic coils discussed herein. Control element 222 can be configured to extend along the exterior of shaft 204 for coupling to controller 112 when suturing device 200 is assembled with scope 102. Reinsertion sheath 204 can thus be configured to fit around control element 222 as depicted in FIG. 2. However, control element 222 can additionally extend through a lumen within shaft 204.

As discussed herein, Suture body 218 can comprise electro-mechanical components that can generate an electro-magnetic field in and between arms 226A and 226B to push and/or pull a magnetic suturing element, e.g., a needle, between suture tracks 228A and 228B.

FIG. 15A is a side schematic view of suturing device 200 of FIG. 14 showing suture body 218 rotated flush with coupler 216 via hinge 225. FIG. 15B is a side schematic view of suturing device 200 of FIG. 14 showing suture body 218 rotated away from coupler 216 via hinge 225. FIGS. 15A and 15B are discussed concurrently.

Housing 220 can be positioned underneath coupler 216 proximal of suture body 218. Housing 220 can comprise control elements, such as electronics, a motor, a power source and the like, for elements of suture body 218. Control element 222 (FIG. 14) can extend proximally from housing 220 to connect suture body 218 to a controller. Housing 220 can additionally include stores of suturing material and components for tying-off or anchoring the suturing material. Suture body 218 can be rotatably coupled to coupler 216 via hinge 225. Shaft 204 of endoscope 202 (FIG. 14) can extend into channel 224 of coupler 216. Distal face 206 of shaft 204 can be exposed distally to the exterior of coupler 216 so as to have a view of space 230.

With reference to FIG. 15A, scope 202 can be more easily navigated through anatomy with suture body 218 rotated into engagement with face 206 of shaft 204. Thus, arms 226A and 226B are not protruding distally of face 206 and potentially interfering with operation of imaging component 210 and illumination component 212 for navigation purposes. However, space 230 between arms 226A and 226B can be positioned adjacent face 206 to allow imaging component 210 and illumination component 212 to have visibility beyond suture body 218.

With reference to FIG. 15B, once navigated to the desired location of target tissue within anatomy, suture body 218 can be rotated at hinge 225 to extend arms 226A and 226B outward in front of face 206. As such, without the need to navigate shaft 204, imaging component 210 and illumination component 212 can interact with target tissue between arms 226A and 226B. Suturing device 200 can include a motor to provide rotational input to suture body 218 at hinge 225. The motor can be connected to control element 222 so that an operator of scope 204 can selectively operate the motor to raise and lower suture body 218.

Figure 16:
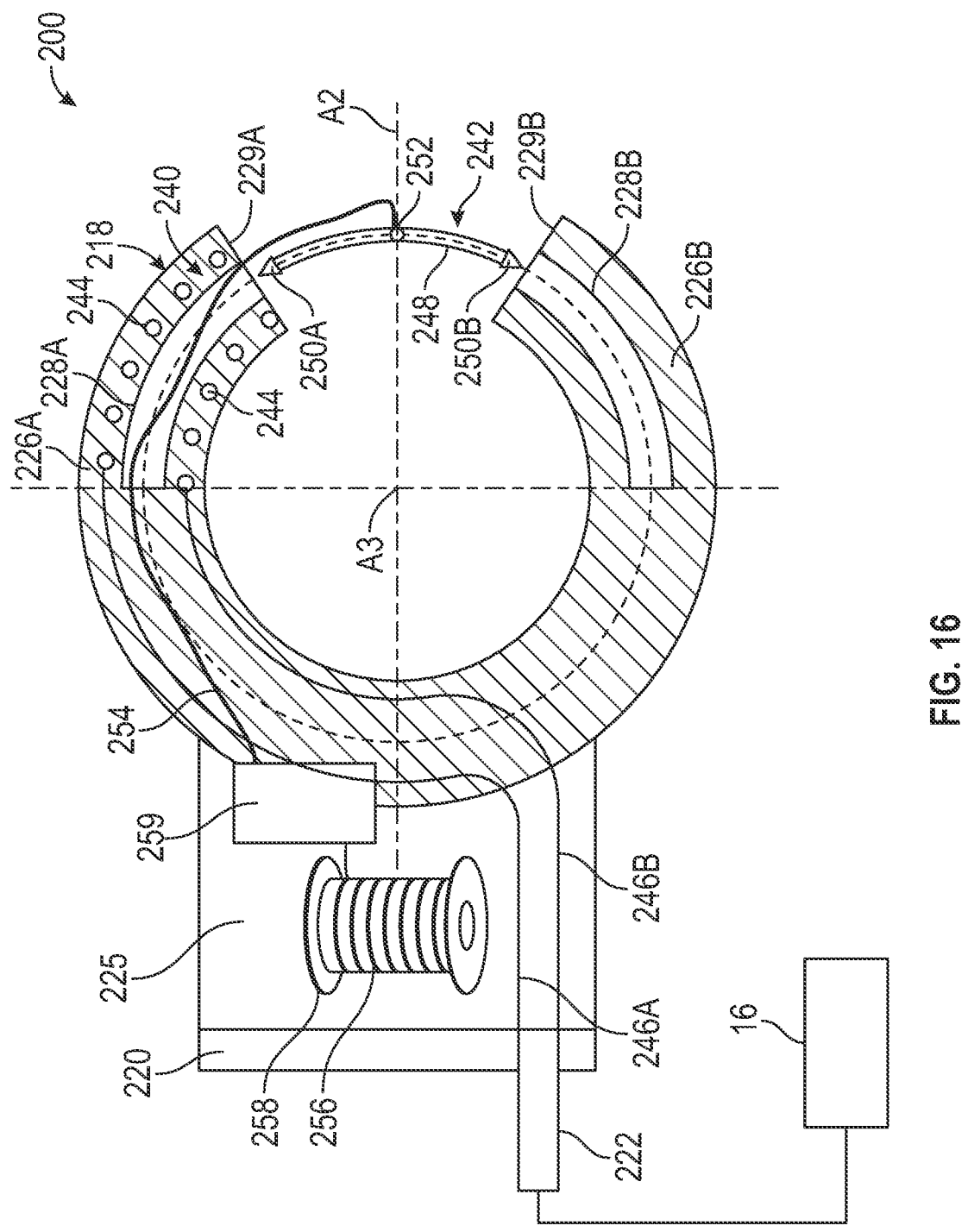
FIG. 16 is a schematic cross-sectional view of a electro-magnetic suturing mechanism of the present disclosure comprising an arcuate suturing element disposed between arcuate tracks.

FIG. 16 is a schematic cross-sectional view of electro-magnetic suturing mechanism 240 of suturing device 200 the present disclosure comprising arcuate suturing element 242 disposed in between arcuate tracks 228A and 228B and coil 244. Coil 244 can comprise leads 246A and 246B. Suturing element 242 can comprise body 248, tips 250A and 250B and eyelet 252. Suturing element 242 can be connected to suture material 254. Windings 256 of suture material 254 can be stored on spool 258. Closure device 259 can be positioned on suturing device 200 to receive suture material 254 from spool 258. Closure device 259 can be configured to attach a component (e.g., an anchor) to suture material 254 or impart a characteristic (e.g., a knot) to suture material 254 in order to allow suture material to be cinched onto tissue.

As discussed with reference to FIGS. 17A-17D, suturing element 242 can be moved between tracks 228A and 228B to pull suturing element 242 through tissue. As discussed with reference to FIGS. 18-20, suturing element 242 can be moved between tracks 228A and 228B via various electro-magnetic and mechanical actions to reciprocate or circulate suturing element 242 between tracks 228A and 228B. Suturing tracks 228A and 228B and arms 226A and 226B can comprise arcuate segments so that suture body 218 has "C" shape. In examples, tracks 228A and 228B and arms 226A and 226B can be circle arc segment centered around axis A3. Axis A3 can be perpendicular to axis A2 of coupler 216, which can be coaxial with axis A1 of shaft 204 of scope 202 (FIG. 14).

In the example of FIG. 16, electricity can be provided to coil 244 through leads 246A and 246B from control element 222. Coil 244 can comprise a copper winding over which material of arm 226A is molded. Control element 222 can be coupled to a power source in hinge 225 or proximally in control unit 16. The electricity can pass through coil 244 to generate an electro-magnetic field. The electromagnetic field can be configured to propel suturing element 242 from track 228A toward track 228B. Thus, tip 250B can penetrate tissue and pull suture material 254 through the tissue. Suture material 254 can be attached to suturing element 242 at eyelet 252, which can comprise a bore or another feature to which suture material 254 can be attached. As suturing element 242 is moved, suture material 254 can be pulled off spool 258. Spool 258 can be rotatably mounted in hinge 225, suture body 218 or housing 220. Suturing element 242 can be pushed completely into track 228B. As discussed herein, suturing element 242 can be returned to track 228A via various electro-magnetic or mechanical operations, such via direct electro-magnetic propulsion from a coil in arm 226B, reverse electro-magnetic propulsion from coil 244, mechanical force from arm 226A or mechanical force from arm 226B. Tip 250A can allow suturing element 242 to pierce through tissue upon return to track 228A.

Closure device 259 can be configured to attach an anchor element to suture material 254. In examples, closure device 259 can attach anchor 266 (FIG. 17B), which can comprise a ball of polymeric material clamped onto suture material 254. In additional examples, closure device 259 can comprise a staple that pushes suture material 254 against tissue or a rivet that clasps onto suture material 254.

Suturing element 242 can comprise body 248 having an arcuate shape. The curvature of body 248 can match the curvature of tracks 228A and 228B. However, in other examples, suturing element 242 can be straight and can be of sufficiently short length to fit within the curvature of tracks 228A and 228B. Eyelet 252 is shown be positioned at the middle of body 248. However, eyelet 252 can be positioned elsewhere such as proximate one of tips 250A or 250B. Body 248 can be fabricated of ferromagnetic material in order to interact with the electro-magnetic field of coil 244. Body 248 can be a magnet or magnetized. Body 248 can additionally be fabricated of biocompatible material and/or bioresorbable material.

FIGS. 17A-17D are schematic illustrations of electro-magnetic suturing device 240 of FIG. 16 driving suturing element 242 through tissue 260 to pull suture material 254 into tissue 260 and close incision 262. Incision 262 can be formed between tissue portions 264A and 264B of tissue 260. Tissue 260 can be a duct wall of an anatomic passageway. Incision 262 can be an undesirable perforation through the duct wall that can be closed to prevent bleeding. In another example, tissue portions 264A and 264B can comprise portions of a stomach wall being sutured together to reduce the size of the stomach in a bariatric procedure. For the sake of simplicity, not all elements of electro-magnetic suturing device 240 and suturing device 200 are illustrated in each of FIGS. 17A-17D.

Figures 17A, 17B:
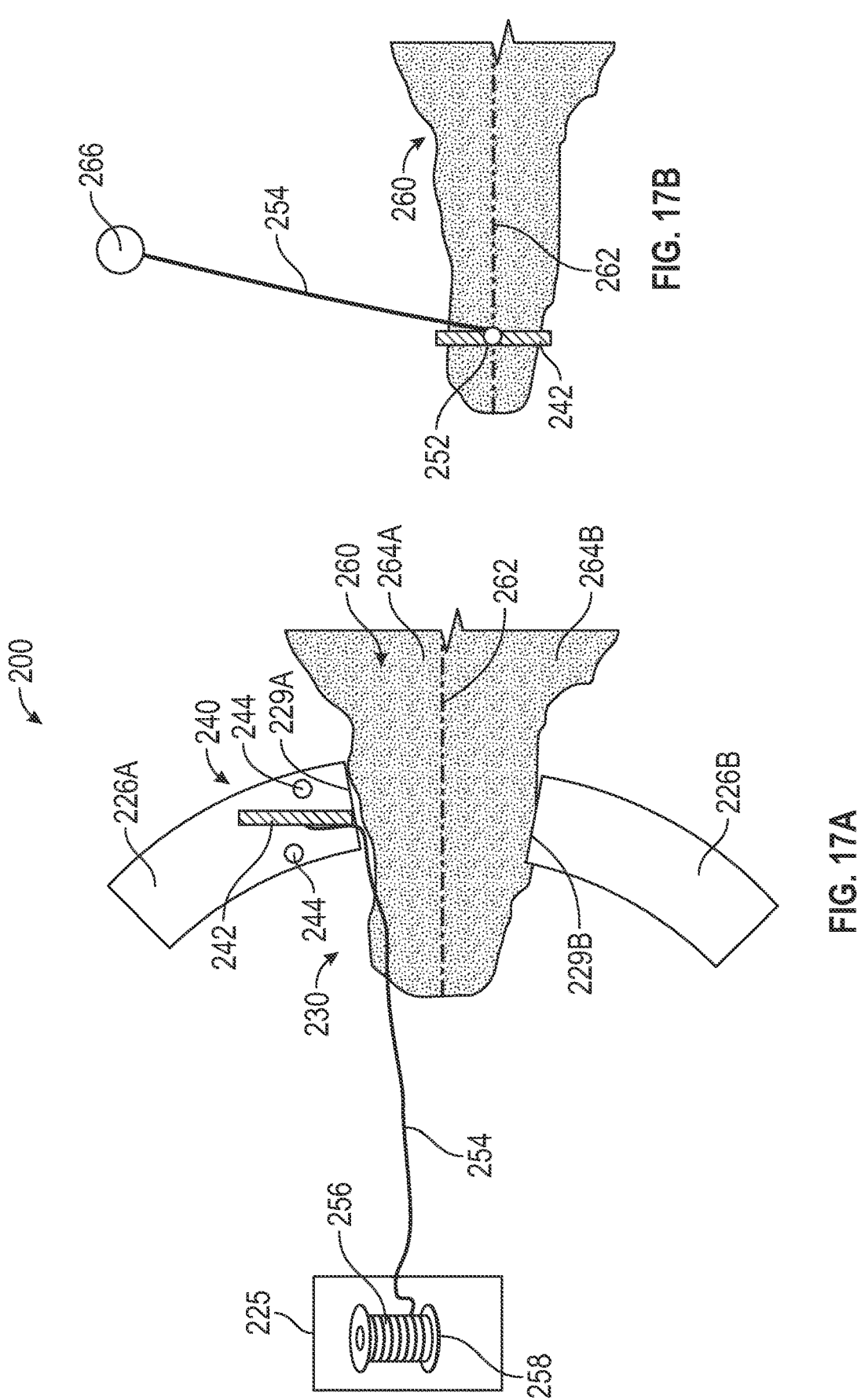
FIGS. 17A-17E are schematic illustrations of an electro-magnetic suturing device of the present disclosure driving a suturing element through tissue to pull suture material into the tissue and close an incision.

In FIG. 17A, tissue 260 is positioned in space 230 between arms 226A and 226B. End faces 229A and 229B can abut tissue 260 to position tracks 228A and 228B (FIG. 16) adjacent the target tissue. Suturing element 242 can be positioned in track 228A (FIG. 16) in arm 226A. Suture material 254 can extend from spool 258 to suturing element 242 via any suitable passage. In examples, spool 258 can be located in hinge 225. Coil 244 can be energized to generate an electro-magnetic field to push suturing element 242 from arm 226A toward arm 226B.

In FIG. 17B, suturing element 242 can be positioned in tissue 260. Suture material 254 can include anchor 266. Anchor 266 can be dispensed by closure device 259 (FIG. 16) as suture material 254 is pulled off of spool 258 (FIG. 17A). Closure device 259 can simultaneously cut suture material 254 from windings 256 of other suture material on spool 258. Thus, a length of suture material 254 can be provided to close incision 262. Suture material 254 can be attached to suturing element 242 via eyelet 252 and a knot or another suitable attachment feature.

Figures 17C, 17D, 17E:
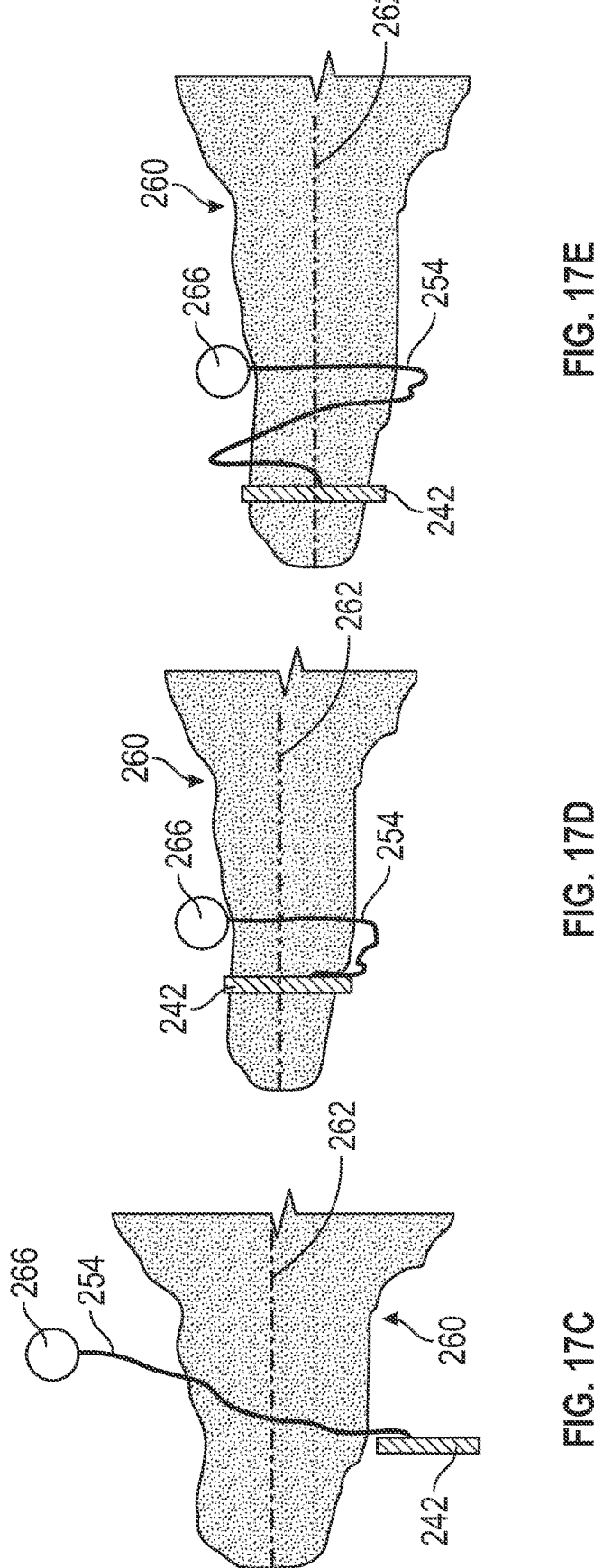

In FIG. 17C, suturing element 242 can be pushed through tissue 260 into arm 226B (FIG. 17A), such as via continued operation of coil 244 to generate an electro-magnetic field. Suture material 254 can follow suturing element 242 so that suture material 254 completes a first pass through tissue 260. As described herein suturing element 242 can additionally be pulled into tissue 260 vie electro-magnetic and/or mechanical means.

In FIG. 17D, suture device 200 can be operated to push suturing element 242 back into and through tissue 260. Suture device 200 can be moved away from where suturing element 242 was initially passed through tissue 260, such as closer to the tip of tissue 260, axially along incision 262. Next, suture device 200 can be activated to move suturing element 242. As is discussed with reference to FIGS. 18-20, suture device 200 can be configured to return suturing element 242 to arm 226A via electro-magnetic force via pushing or pulling or via mechanical force via pushing or pulling. Suture device 200 can be operated to push suturing element 242 through tissue 260 back into arm 226A. Suture material 254 can be pulled to engage anchor 266 with tissue 260.

Figures 18, 19:
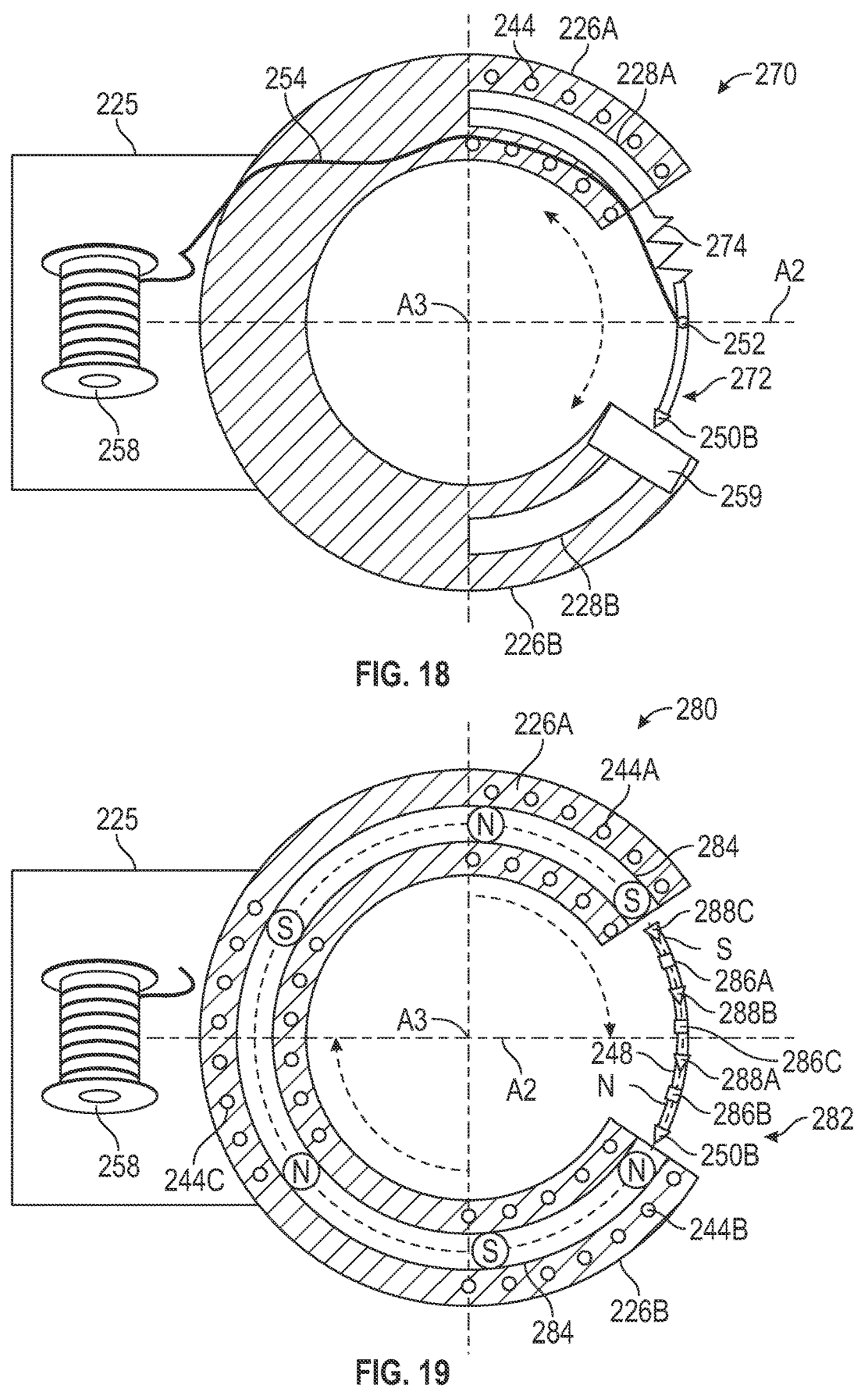

In FIG. 17E, suture device 200 can be operated to tighten suture material 254. Electro-magnetic or mechanical forces can be generated to push and pull suture material 254 to take out the length of slack in suture material 254 shown in FIG. 17B between tissue 260 and anchor 266. Suturing element 242 can be advanced until anchor 266 engages tissue 260. As such, incision 262 between tissue portions 264A and 264B of incision 262 can be pulled to into engagement. At such point, suture material 254 can be released from suture element 242. In examples, one or both of arms 226A and 226B (FIG. 17A) can include a blade or another device to cut suture material 254 away from suture element 242. As shown in FIG. 18, another closure device 278 (FIG. 18) can be provided between arms 226A and 226B to act on suture material 254 to prevent suture material 254 to back out of tissue 260. For example, another anchor 266 could be applied to the end of suture material 254. In additional examples, suture element 242 can be left in tissue 260 to dissolve or resorb into the anatomy.

FIG. 18 is a schematic cross-sectional view of electro-magnetic suturing mechanism 270 of the present disclosure comprising a magnetically-driven and spring-retracted suturing element 272. Suturing mechanism 270 and suturing element 272 of FIG. 18 can be configured similarly as suturing mechanism 240 and suturing element 242 of FIG. 16 with the following variations. Suturing mechanism 270 can include spring 274 to provide mechanical return forces to suturing element 272. Correspondingly, suturing element 272 can include tip 250B at a leading edge and spring 274 can be attached to a trailing end of suturing element body 248. As such, coil 244 can be activated to provide motive force for suturing element 270 from arm 226A toward arm 226B. Spring 274, or another mechanical biasing element, can provide motive force to pull suturing element 270 back to arm 226A. Thus, suturing element 270 can be reciprocated back and forth using electro-magnetic and mechanical activation power.

Suturing mechanism 270 can also include closure device 278. Closure device 278 can be positioned in the path of suturing element 270. In the illustrated example, closure device 278 can be positioned on arm 226B to that suturing element 272 passes through closure device 278 after passing through tissue. Closure device 278 can comprise a device for facilitating attachment of suture material 254 to tissue 260. In an example, closure device 278 can apply heat to suture material to cause melting of the material to join suture material 254 with another strand of suture material. In an example, closure device 278 can apply an anchor to suture material 254, such as anchor 266 or another element. In an additional example, closure device 278 can attach another strand of suture material to suture material 254 in a similar manner as a sewing machine. Closure device 278 can be used with any of the suturing mechanisms of FIGS. 16, 19 and 20. Thus, in examples, after coil 244 pushes suturing element 270 into tissue, closure device 278 can apply an anchor to suture material 254 on the return stroke of suturing element 270 to prevent suture material 254 from being pulled back through the tissue. Thus, suture material 254 can be attached to suture element 270 close to tip 250B and suture element 270 need not completely pass through the tissue, such as at where spring 274 attaches thereto.

FIG. 19 is a schematic cross-sectional view of electro-magnetic suturing mechanism 280 of the present disclosure comprising magnetically-circulated suturing element 282. Suturing mechanism 280 and suturing element 282 of FIG. 19 can be configured similarly as suturing mechanism 240 and suturing element 242 of FIG. 16 with the following variations. Suturing mechanism 280 can include first coil 244A, second coil 244B and third coil 244C to provide electro-magnetic circulatory movement forces to suturing element 282 in circular track 284 and suturing element 282 can comprise magnetic elements 286A-286C and barbs 288A-288C. Circular track 284 can replace tracks 228A and 228B.

In examples, one, two or three of coils 244A-244C can be activated to actuate suturing element 282. As discussed below, coils 244A-244C can be operated to provide various combinations of pushing and pulling of suturing element 282. Control unit 16 (FIG. 14) can be connected to coils 244A-244C operate coils 244A-244C in various modes to control the timing of activation of coils 244A-244C and the north (N)— south (S) direction of the poles of the magnetic fields generated thereby to drive suturing element 282. Thus, control unit 16 can be programmed with instructions for operating coils 244A-244C in multiple operating modes and an operator of suturing mechanism 280 can, at controller 112, select one or more modes to operate suturing element 282, including selecting whether to drive suturing element in forward or backward directions.

In examples, coils 244A and 244B can be activated to produce magnetic pushing forces on suturing element 282. Thus, coil 244A can be activated to push suturing element 282 toward arm 226B and coil 244B can be sequentially or simultaneously activated to generate another magnetic force to continue to push suturing element 282 further into track 284 toward arm 226A. As such, suturing element 282 can be continuously pushed by magnetic fields generated by coils 244A and 244B. Thus, coils can be arranged to produce magnetic fields having north and south poles oriented in the same direction, as indicated in FIG. 19. Coil 244C can likewise be activated to push suturing element 282 in the clockwise direction.

In examples, coils 244A and 244B can be activated to produce magnetic pushing and pulling forces on suturing element 282. Thus, coil 244A can likewise be activated to push suturing element 282 toward arm 226B (clock-wise force) and coil 244B can be simultaneously activated to generate another magnetic force to pull suturing element 282 into arm 226B (clock-wise force). Once suturing element 282 is within arm 226B and suitably positioned relative to coil 244B (e.g., past soil 244B), coil 244B can be switched to producing a magnetic pushing force (clock-wise force) and coil 244A can be switched to producing a magnetic pulling force (clock-wise). Activation of coils 244A and 244B can be programmed and coordinated to maximize motive forces applied to suturing element 282. In an example, 1) coil 244A can be activated to produce pushing forces and coil 244B can be activated to produce pulling forces, 2) coil 244B can be activated to produce pushing forces, 3) coil 244A can be activated to produce pulling forces, and 4) steps 1)-3) are repeated. Coil 244C can likewise be activated to switch between pulling and pushing suturing element 282 as suturing element approaches and leaves coil 244C.

Body 248 can include magnetic elements 286A-286C can comprise magnetic bodies that can interact with magnetic fields generated by coils 244A and 244B. Magnetic elements 286A-286C can be configured to have magnetic fields that are opposite to the magnetic fields generated by coils 244A and 244B. Thus, as coils 244A and 244B are activated, suturing element 282 can be further propelled by interaction of the magnetic fields of magnetic elements 286A-286C of with the magnetic fields of coils 244A and 244B. In examples, coil 244A can be configured to produce a magnetic field with the north pole N1 at the top and the south pole Si at the bottom, relative to the orientation of FIG. 19, coil 244B can be configured to produce a magnetic field with the north pole N2 at the bottom and the south pole Si at the top, relative to the orientation of FIG. 19, and magnetic elements 286A-286C can be configured to produce a magnetic field with the north pole N3 at the bottom and the south pole S at the top, relative to the orientation of FIG. 19. In examples, magnetic elements 286A-286C can be made of diamagnetic material that is repelled by a magnetic field.

Body 248 can additionally include barbs 288A-288C to prevent suturing element 282 from migrating backward in tissue. Barbs 288A-288C can comprise micro-hooks, barbs or fish scales that can readily pass through tissue in the clockwise direction, but that cannot readily pass through tissue in the counterclockwise direction. Barbs 288A-288C can extend radially outward of body 248 and can be flared outward therefrom.

In examples, circular track 284 can be configured in the shape of an infinity symbol. As such, circular track 284 can be rotated along axis A2 such that track 226A is further into the plane of FIG. 19 and track 226B is further out of the plane of FIG. 19. A second occurrence of track 284 can be superimposed thereon to intersect track 284 along axis A2 proximate spool 258, but can be rotated such that the track equivalent to track 226A is further out of the plane of FIG. 19 and the track equivalent to track 226B can be further into the plane of FIG. 19. Thus, suturing element 282 can be configured to move out of the plane of FIG. 19 to provide three-dimensional suturing to tissue.

Figure 20:
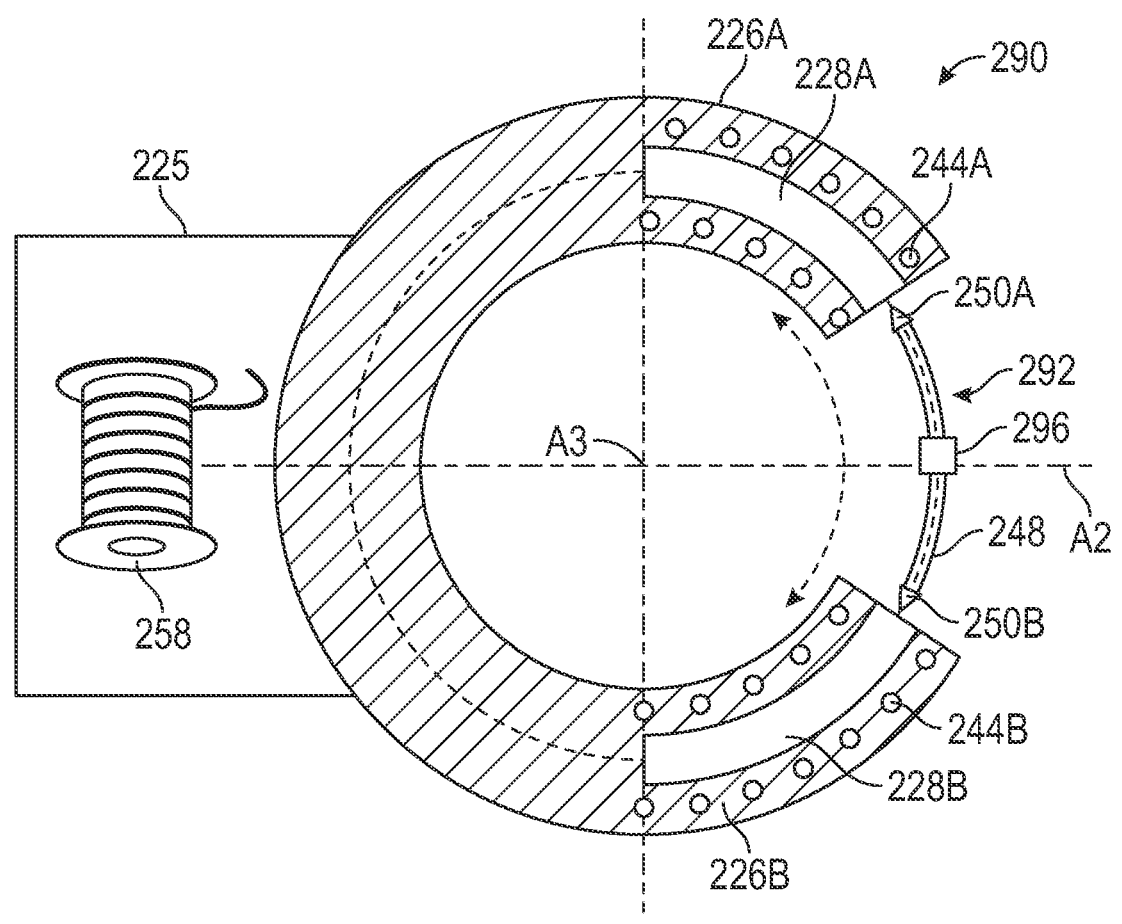
FIG. 20 is a schematic cross-sectional view of a electro-magnetic suturing mechanism of the present disclosure comprising a magnetically-reciprocated suturing element.

FIG. 20 is a schematic cross-sectional view of electromagnetic suturing mechanism 290 of the present disclosure comprising magnetically-reciprocated suturing element 292. Suturing mechanism 290 and suturing element 292 of FIG. 20 can be configured similarly as suturing mechanism 240 and suturing element 242 of FIG. 16 with the following variations. Suturing mechanism 290 can include coils 244A and 244B and suturing element 292 can comprise magnetic element 296.

Coils 244A and 244B can be configured to reciprocate suturing element 292. In examples, coils 244A and 244B can be activated to produce magnetic pushing and pulling forces on suturing element 282. Thus, coil 244A can be activated to push suturing element 282 toward arm 226B (clock-wise force) and coil 244B can be simultaneously activated to generate another magnetic force to pull suturing element 282 into arm 226B (clock-wise force). Once suturing element 282 is within arm 226B, coil 244B can be switched to producing a magnetic pushing force (counter-clockwise force) and coil 244A can be switched to producing a magnetic pulling force (counter-clockwise force). Activation of coils 244A and 244B can be programmed and coordinated to maximize motive forces applied to suturing element 282. In an example, 1) coil 244A can be activated to produce pushing forces and coil 244B can be activated to produce pulling forces, 2) coil 244B can be activated to produce pushing forces, 3) coil 244A can be activated to produce pulling forces, and 4) steps 1)-3) are repeated.

Magnetic element 296 can comprise a magnetic body that can interact with magnetic fields generated by coils 244A and 244B, similar to those describe with reference to FIG. 19. Thus, magnetic element 296 can be propelled by electromagnetic fields generated by coils 244A and 244B. In examples, magnetic element 296 can be made of diamagnetic material that is repelled by a magnetic field.

Figure 21:
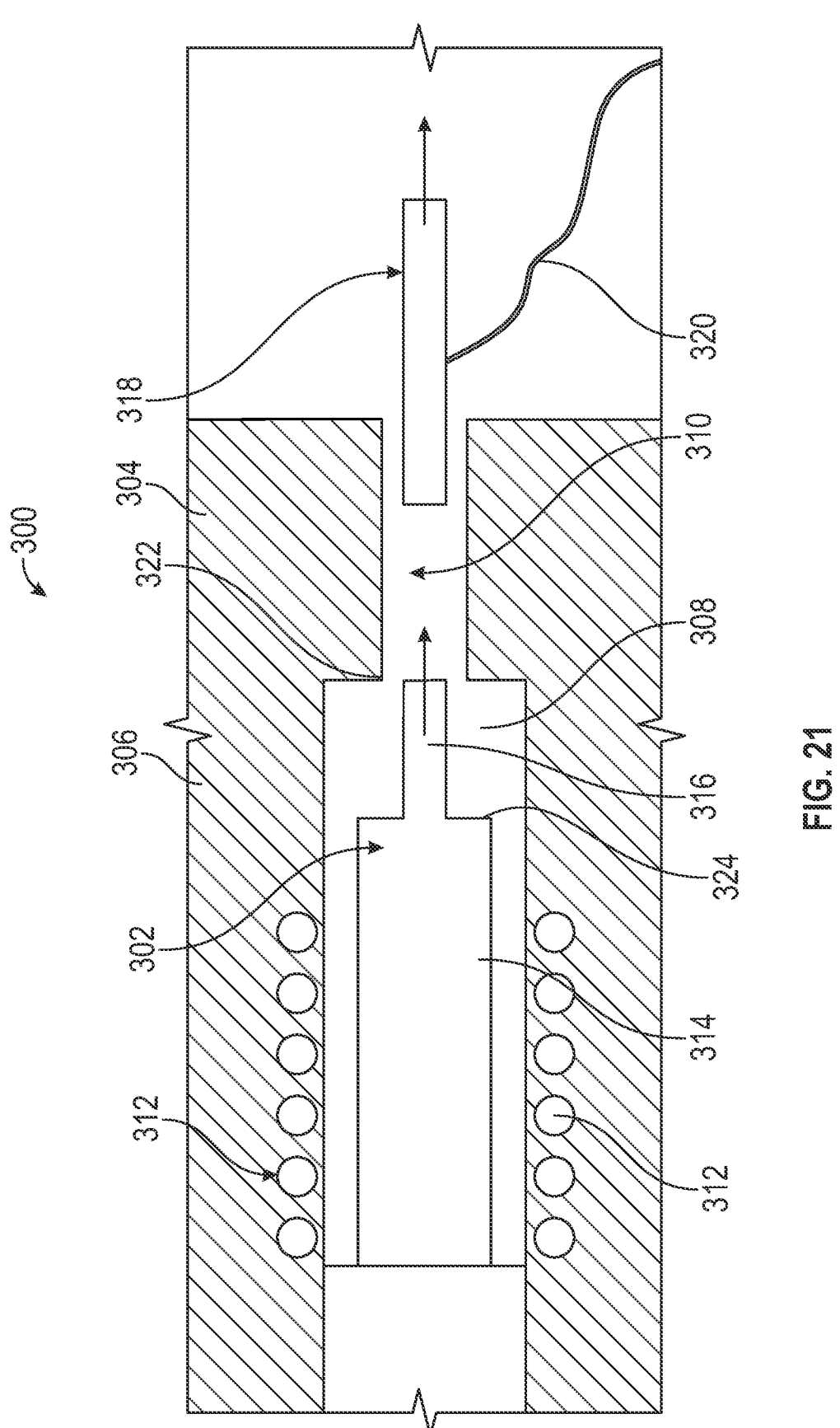
FIG. 21 is a schematic cross-sectional view of a electro-magnetic suturing mechanism of the present disclosure comprising a magnetically-driven hammer.
Figure 23:
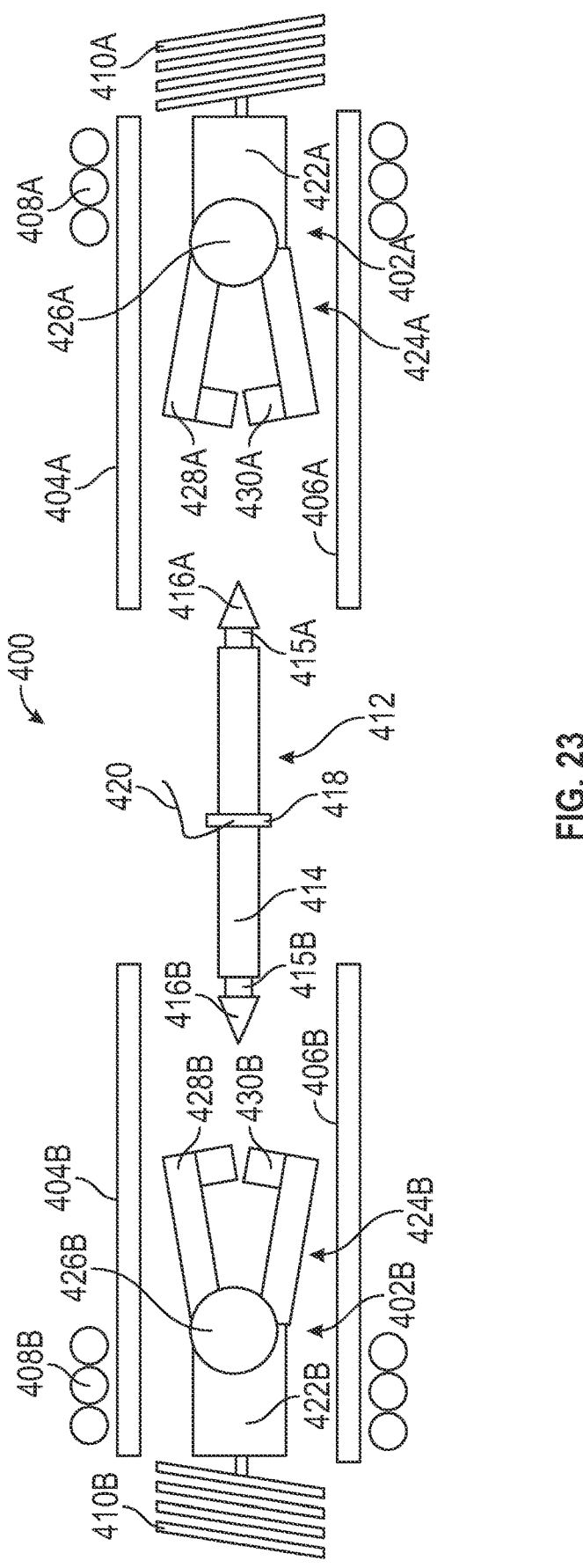
FIG. 23 is a schematic cross-sectional view of a electro-magnetic suturing mechanism of the present disclosure comprising a magnetically-driven shuttle.

FIGS. 21-23 illustrate additional examples of electric suturing devices. The devices of FIGS. 21-23 can be particularly suitable for use in laparoscopic procedures, cut can be used in other procedures, such as endoscopy procedures. For example, laparoscopic procedures can involve using an incision in anatomy to insert the scope. Such incisions can allow for the larger instruments as compared to orally inserted scopes, for example. Example laparoscopic procedures include gallbladder removal (cholecystectomy), appendectomy, hernia repair, removal of part of the colon (colectomy) or small intestine, surgery for acid-reflux disease (fundoplication), removal of adrenal glands, and removal of the spleen. Some of these procedures can involve the production of internal incisions or cutting that can be closed with suturing. In some situations, it can be advantageous to push two pieces of tissue into engagement for suturing together. As such, laparoscopes can be more robust and can involve the sue of pivotable jaws that grab tissue for suturing, as discussed below.

FIG. 21 is a schematic cross-sectional view of electromagnetic suturing mechanism 300 of the present disclosure comprising magnetically-driven hammer 302. Suturing mechanism 300 can comprise suture body 304 comprising arm 306, hammer chamber 308, suture element chamber 310 and coil 312. Hammer 302 can comprise driving mass 314 and driver 316. Suturing element 318 can be connected to suture material 320.

Suture body 304 can comprise a portion of suture body 218 (FIG. 14). Suture body 304 can define hammer chamber 308 and suture element chamber 310. Hammer chamber 308 can be configured to slidably receive driving mass 314. Driving mass 314 can comprise a mass of material having a large mass relative to the mass of suturing element 318 to facilitate transfer of kinetic energy from hammer 302 to suturing element 318. Driver 316 can extend from driving mass 314 into suture element chamber 310. Suture element chamber 310 can be configured to slidably receive driver 316. Suture element chamber 310 and driver 316 can be radially smaller than driving mass 314 and hammer chamber 308 to form shoulder 322. Thus, end face 324 of driving mass 314 can impact shoulder 322 to prevent hammer 302 from being displaced from hammer chamber 308. However, driver 316 can be configured to penetrate into suture element chamber 310 to contact suture element 318.

Coil 312 can be activated with electrical energy to generate an electro-magnetic field to push hammer 302 to the right in FIG. 21. Driver 316 can be configured to strike suture element 318 to push suture element 318 to the right. Face 324 of driving mass 314 can impact shoulder 322, while suture element 318 can continue to be driven to the right. Thus, suture element 318 can be driven by momentum through tissue. In other examples, driver 316 can be longer so as to be configured to directly drive suture element 318 through tissue. Hammer 302 can be returned to the left-hand position via a mechanical element such as a spring or via electro-magnetic activation from coil 312 in the opposite direction. Suture element 318 can be driven back to the left-hand position via any suitable methods including those described herein. In examples, a spring connected to the right-hand side of suture element 318 can push suture element to the left. In examples, another coil in suture body 304 can electro-magnetically push suture element 318 to the left.

In examples, driver 316 can comprise a rigid and solid body that can coaxially align with suture element 318 and suture element chamber 310. In additional examples, driver 316 can be curved or arcuate so as to function with correspondingly curved suture element chamber 310 and suture element 318. In examples, driver 316 can be flexible to operate with examples of suture element chamber 310 that are oblique to the central axis of hammer 302. In examples, driving mass 314 can be fabricated of metal, such as steel, and driver 316 can be fabricated from plastic, such as PVC, polyethylene, PPEK and polypropylene. The metal component can thus be made of a more dense material to provide the driving force and the plastic component can be made to bend as needed to guide the suturing element.

FIG. 22 is a schematic cross-sectional view of electro-magnetic suturing mechanisms 300A and 300B and magnetically-driven hammers 302A and 302B used with suturing device 330 having arms 332A and 332B. Arm 332A can comprise aligned channel 334A and oblique channel 336A. Arm 332B can comprise aligned channel 334B and oblique channel 336B. Although not shown in FIG. 22, arms 332A and 332B can be coupled at ends opposite oblique channels 336A and 336B. In examples, arms 332A and 332B can be pivotably or rotatably coupled, such as via a hinge mechanism. In examples, arms 332A and 332B can be rotated such that oblique channels 336A and 336B are brought closer to each other. Thus, portions of arms 332A and 332B forming oblique channels 336A and 336B can be rotated toward each other to grab or push tissue to be sutured. In examples, arms 332A and 332B can be manually rotated, such as by using a scissor mechanism operated by pull-strings or cables. In examples, arms 332A and 332B can be electrically rotated using one or more motors operable from a proximal end of a scope.

Aligned channel 334A can be coaxially aligned with driving mass 314A and aligned channel 334B can be coaxially aligned with driving mass 314B. Oblique channel 336A can be oblique to the axis of driving mass 314A and oblique channel 336B can be oblique to the axis of driving mass 314B. Driver 316A can be flexible to extend between aligned channel 334A and oblique channel 336A. Driver 316B can be flexible to extend between aligned channel 334B and oblique channel 336B. Thus, drivers 316A and 316B can be withdrawn into aligned channels 334A and 334B to be completely straight. Driving masses 314A and

314B can be driven forward within aligned channels 334A and 334B to push drivers 316A and 316B at least partially into oblique channels 336A and 336B. Drivers 316A and 316B can change shape while being extend in and out of oblique channels 336A and 336B. Drivers 316A and 316B or portions thereof can thus align with suturing element 318 when positioned within oblique channels 336A and 336B. Oblique channels 336A and 336B are illustrated as being straight segments disposed at approximately ninety-degree angles relative to aligned channels 334A and 334B. However, oblique channels 336A and 336B can be disposed at other angles and can be curved.

Coils 312A and 312B can be activated to alternately act on hammers 302A and 302B to reciprocate suturing element 318. Coil 312A can be activated to push suturing element 318 toward arm 332B. The distal tip of driver 316A can include a cup-shaped feature or socket to receive tip 338A of suturing element 318 to prevent dulling or blunting of a sharp tip used to penetrate tissue. Stop 342A can be used to prevent driving mass 314A from traveling too far within arm 332A, such as into oblique channel 336A. Suturing element 318 can be pushed through tissue by direct driving of driver 316A and energy from driving mass 314A. Thus, driver 318A can have approximately the same diameter or a smaller diameter as suturing element 318 so as to be able to be pushed through the puncture in tissue produced by suturing element 318. In other examples, driver 318A does not continue into tissue and suturing element 318 can continue through tissue via momentum. Suturing element 318 can thus be pushed into arm 332B. Spring 342A can be used to return driver 318A to be contracted into arm 332A. Within arm 332B, suturing element 318 can engage driver 318B. The distal tip of driver 316B can include a cup-shaped feature or socket to receive tip 338B of suturing element 318 to prevent dulling or blunting of a sharp tip used to penetrate tissue. Coil 312B can be activated to push suturing element 318 toward arm 332A. Stop 342B can be used to prevent driving mass 314B from traveling too far within arm 332B, such as into oblique channel 336B. Spring 342B can be used to return driver 318A to be contracted into arm 332A.

Suturing device 330 can be used to motivate hammers 302A and 302B using any of the electro-magnetic devices described herein to electro-magnetically push and pull hammers 302A and 302B and/or mechanically push and pull hammers 302A and 302B. Additionally, suturing device 330 can include closure devices 259 and 278 described herein to attach anchors or other immobilizing qualities to suture material.

FIG. 23 is a schematic cross-sectional view of electro-magnetic suturing mechanism 400 of the present disclosure comprising magnetically-driven shuttles 402A and 402B. Suturing mechanism 400 can comprise first arm 404A and second arm 404B that form channels 406A and 406B, respectively. Coils 408A and 408B can be positioned at arms 404A and 404B, respectively, and springs 410A and 410B can be positioned within channels 406A and 406B to interact with shuttles 402A and 402B, respectively. Suturing mechanism can further comprise suturing element 412, which can comprise body 414, notches 415A and 415B, tips 416A and 416B and coupler 418 for connecting to suture material 420. Shuttles 402A and 402B can comprise masses 422A and 422B and jaws 424A and 424B. Jaws 424A and 424B can comprise hinge 426A, extensions 428A and teeth 430A and hinge 426B, extensions 428B and teeth 430B, respectively.

Arms 404A and 404B can be incorporated into a suturing device described herein and can thus be located in a device attachable to an end of a scope to push and pull suturing element 412 through tissue. Coils 408A and 408B can be embedded within material of arms 404A and 404B or can be covered with an appropriate sheath or the like. Coils 408A and 408B can comprise copper winding in which electric current can be passed to generate magneto-electric fields to drive masses 422A and 422B, respectively. In examples, masses 422A and 422B can be made of ferromagnetic material.

Channels 406A and 406B can be positioned within arms 404A and 404B, respectively, to receive suturing element 412. Channels 406A and 406B can be provided with appropriate stops (not shown) to prevent shuttles 402A and 402B from being propelled out of arms 404A and 404B by the electro-magnetic fields of coils 408A and 408B, respectively. Additionally, springs 410A and 410B, or other biasing elements, can be used to prevent shuttles 402A and 402B from being displaced out of channels 406A and 406B. Furthermore, springs 410A and 410B can be used to retract shuttles 402A and 402B back into arms 404A and 404B after propulsion by coils 408A and 408B.

Shuttles can be pushed and pulled from channels 406A and 406B to reciprocate suturing element 412 through tissue similar to the method described with reference to FIGS. 17A-17D. However, instead of the magneto-electric fields of coils 408A and 408B directly propelling suturing element 412, suturing element is indirectly driven by shuttles 402A and 402B, which are directly driven by the magneto-electric fields of coils 408A and 408B. Shuttles 402A and 402B can be driven such that the momentum of masses 422A and 422B can be used to push suturing element 412.

Suturing element 412 can be positioned between opposing teeth 430A in extensions 428A. Teeth 430A can be positioned in notch 415A to grab ahold of suturing element 412. Extensions 428A can be rotated inward by interaction with wall of channels 406A and 406B. Hinge 426A can be biased to open or spread apart teeth 430A. Thus, when shuttle 402A is propelled leftward in FIG. 23, extensions 428A can spring open to release suturing element 412. However, the momentum of suturing element 412 will maintain leftward momentum of suturing element 412 through tissue an into shuttle 402B. Shuttle 402B can be waiting to receive suturing element 412 with extensions 428B spread open to receive suturing element 412. As such, operation of shuttles 402A and 402B can be coordinated, such as by control unit 16 (FIG. 3), to reciprocate suturing element 412. For example, 1) shuttle 402A can be propelled leftward by operation of coil 408A to push suturing element leftward, 2) coil 408B can be simultaneously propelled rightward to receive suturing element 412, 3) coil 408B can be deenergized to retract into channel 406B via operation of spring 410B, 4) coil 408A can maintain energization to keep extensions in position to receive suturing element 412, 5) coil 408B can be energized to push suturing element 412 forward into shuttle 402A, and steps 1-5 can be repeated.

In additional examples, suturing element 412 can be driven between teeth 430A and 430B to spread apart extensions 428A and 428B to allow teeth 430A and 430B to enter notches 415A and 415B. Thus, shuttles 402A and 402B can return to the retracted positions within channels 406A and 406B to receive suturing element 412.

In view of the foregoing, suturing element 412 can be driven through tissue to pull suture material 420 into the tissue. Because suturing element 412 need not magnetically interact with the magnetic fields of coils 408A and 408B, suturing element 412 can be made of any desirable material suitable for suturing in a biological environment.

Figure 24:
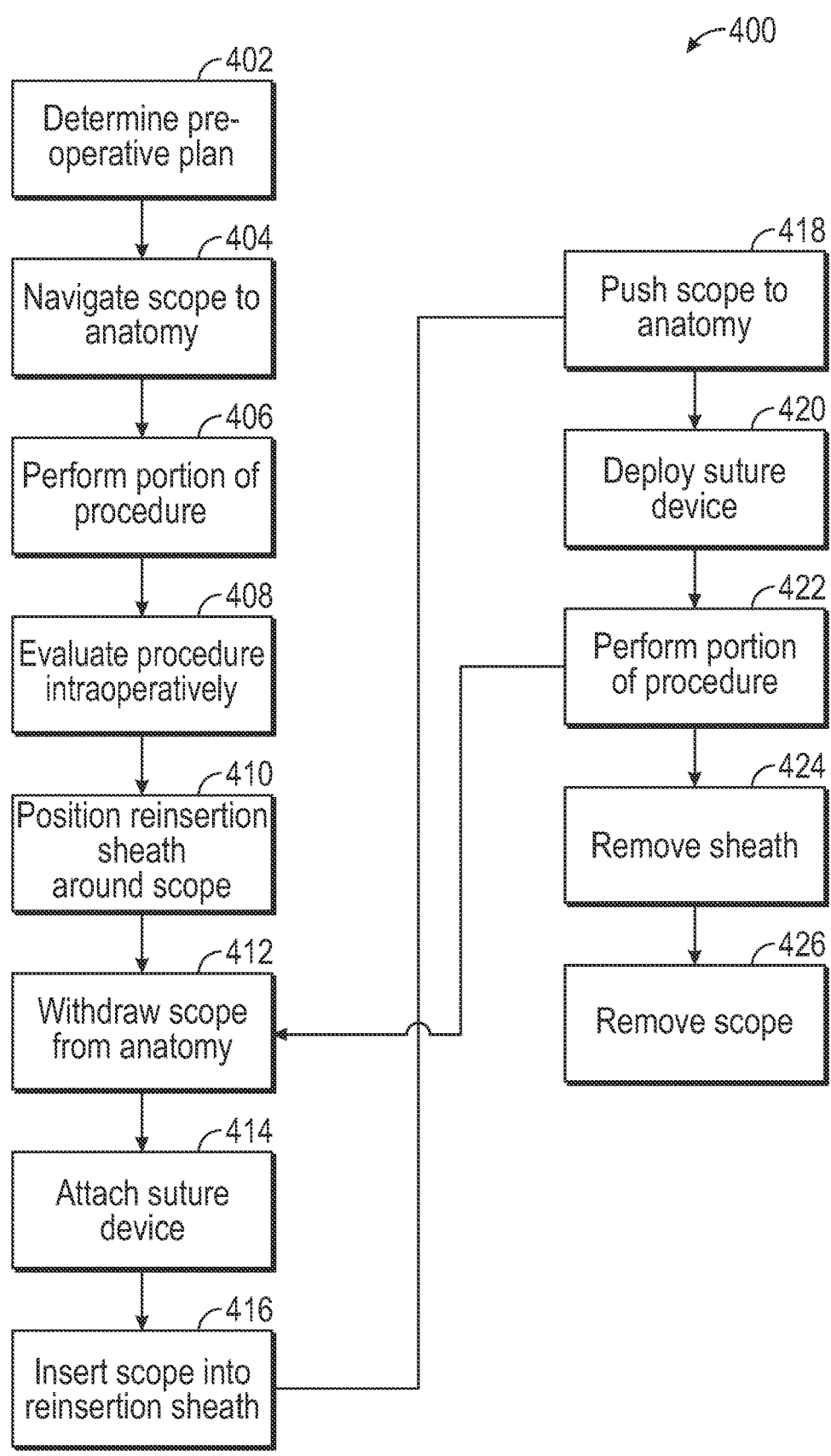
FIG. 24 is a block diagram illustrating methods of suturing tissuing using scopes, reinsertion sheaths and suturing attachments of the present disclosure.

FIG. 24 is a block diagram illustrating methods 400 of suturing tissuing using scopes, reinsertion sheaths and suturing attachments of the present disclosure. Methods 400 can encompass the use of scope 102, reinsertion sheath 104, tissue separator device 106 and suturing attachment 108 of FIGS. 1 and 2, as well as any of the devices described herein.

At step 402, a patient can be evaluated for the performance of a medical procedure. In an example, it can be determined pre-operatively that the colon of the patient is to be treated with a tissue collector device, such as tissue separator device 106 (FIG. 1). The treatment can include the removal of diseased or other tissue. It can be determined preoperatively that the tissue can be collected without the need for incising, cutting or puncturing a duct wall of the patient. Thus, it can be determined preoperatively that the procedure will not involve suturing. The pre-operative plan can thus not involve attaching a suturing device, such as suture device 108 (FIG. 1) to a scope to be used to perform the procedure, such as scope 102 (FIG. 1).

At step 404, a scope can be navigated through anatomy to the tissue of interest. An access portal or incision can be made in anatomy of the patient. In examples, scope 102 (FIG. 1) can be inserted into the patient and guided to a colon. Steering and navigation features of scope 102 can be employed to guide the distal end of scope 102 to target tissue. For example, imaging capabilities can be used to visualize anatomy including intersections of anatomical ducts. Steering capabilities can be used to turn the distal end of scope 102 into the desired duct and the target tissue within the desired duct.

At step 406, a portion of the medical procedure can be performed. For example, a portion of the procedure planned preoperatively at step 402 can be performed. Target tissue can be collected using tissue separator device 106. The target tissue can comprise tissue that is potentially diseased or otherwise indicative of a diseased condition of the patient. For example, separators 138A and 138B can be manipulated from control device 134 to engage target tissue one or more times to collect, separate if necessary, and store target tissue.

At step 408, the procedure being performed can be evaluated. For example, the total amount of tissue collected can be evaluated to see if a sufficient quantity has been collected. Also, the patient can be evaluated to determine if all of the diseased tissue has been collected. During the evaluation procedure, the anatomy of the patent can be reviewed to determine if any bleeding is occurring. If bleeding is occurring, it can be determined that a duct wall of the anatomy has been punctured. As such, it can be determined that an incision in the patient is to be closed, such as with a suturing device. Thus, it can be determined that scope 102 is to be withdrawn from the anatomy to facilitate insertion of a suturing device.

At step 410, a reinsertion sheath can be applied to scope 102 while scope 102 remains inserted into anatomy of the patient. As discussed herein, reinsertion sheath 104 can be manipulated to enlarge slit 126, such as by pulling end faces of flanges 128A and 128B (FIG. 7) apart in a circumferential direction. Thus, reinsertion sheath 104 can be moved radially over the proximal portion of shaft 110 (FIG. 2) of endoscope 102. Reinsertion sheath 104 can be relaxed to allow end faces of flanges 128A and 128B to be brought closer together. Additionally, reinsertion sheath 104 can be axially expanded to be inserted into the anatomy. For example, reinsertion sheath 104 can be converted from the compacted configuration of FIG. 8A to the expanded configuration of FIG. 8B in order to allow one of ends 150 or 152 (FIG. 6) to reach the target anatomy by being slid along scope 102. Reinsertion sheath 104 can be gently guided along shaft 110 to not impact the neighboring anatomy or features of scope 102. An axial closure mechanism, such as zipper closure mechanism 182 (FIG. 11) or interlocking rail closure mechanism 192 (FIG. 12), can be used to close slit 126. The axial closure mechanism can be employed before or during axial deployment of the reinsertion sheath.

At step 412, the scope can be withdrawn from the reinsertion sheath. For example, scope 102 can be withdrawn from the anatomy through reinsertion sheath 104. Reinsertion sheath 104 can remain in the anatomy to radially hold open a passage or tunnel to the target anatomy.

At step 414, an attachment can be coupled to the withdrawn scope. An attachment that has been decided to be used at step 408 can be assembled to the scope. For example, suture device 108 can be attached to shaft 110 of scope 102. With reference to FIG. 14, shaft 204 of scope 202 can be inserted into channel 224 of coupler 216 such that end face 206 is proximate suture body 218.

At step 416, the scope along with the attachment device can be inserted into the reinsertion sheath. Scope 102 with suture device 108 can be slide into lumen 124 (FIG. 1) of reinsertion sheath 104.

At step 418, the scope can be pushed into the reinsertion sheath to reach the target anatomy. Scope 102 can be inserted until the distal end face and suture device 108 reach the target anatomy at the distal end of reinsertion sheath 104.

At step 420, the attachment device assembled with the scope at step 414 can be deployed for use. For example, suture housing 218 can be rotated at hinge 225 from the stowed position of FIG. 15A to the deployed position of FIG. 15B. In the stowed position, suture housing 218 can be made to have a smaller footprint to allow for easier insertion of scope 102 through reinsertion sheath 104. However, in the deployed position, suture housing 218 can be extended distally of scope 102 for use.

At step 422, another portion of the surgical procedure planned at step 402 and evaluated at step 408 can be performed. For example, suture device 108 can be used to close an incision and stop bleeding. Any of the various electro-magnetic coils described herein can be activated to provide an electro-magnetic propulsion force either directly to a suturing element or to a hammer or shuttle configured to drive the suturing element. Furthermore, tissue separator device 106 can be used with scope 102 to remove additional tissue from the anatomy. Tissue separator device 106 can be inserted into lumen 119 (FIG. 1) and extended out the distal end of shaft 110 while suture device 108 is attached thereto. Thus, separators 138A and 138B can be positioned within socket 230 of suture housing 218 for use.

Thereafter, method 400 can return to step 412, if desired, to remove the scope and the attachment device and reinsert the scope with a different reattachment device, or can continue to step 424 to complete the operation.

At step 424, the reinsertion sheath can be removed from the scope. For example, reinsertion sheath 104 can be slid proximally along shaft 110 of scope 102 until removed from the anatomy. Reinsertion sheath 104 can be opened at slit 126 to be pulled off of scope 102.

At step 426, the scope can be removed from the anatomy. For example, scope 102 can be pulled out of the anatomy. Alternatively, reinsertion sheath 104 and scope 102 can be removed together or scope 102 can be removed first and insertion sheath 104 removed second. Thereafter, the access portal in the patient can be appropriately closed.

As such, method 400 illustrates examples of methods of performing a medical procedure using a scope that can be withdrawn and reinserted into anatomy of a patient via an intraoperative reinsertion sheath that can be positioned around an in situ scope. The scope can be withdrawn intraoperatively to attach a supplemental device, such as the suturing devices disclosed herein, to perform intraoperatively determined ancillary procedures, such as suturing of an incision. As such, preoperative planning can be simplified because the need to decide a priori whether or not to use an ancillary device, such as a suturing attachment can be deferred to an intraoperative decision. The intraoperative change in procedure can be facilitated by the use of a reinsertion sheath that can be placed around a shaft of a scope already placed into anatomy of a patient, such as through the use of an axially extending slit extending along the reinsertion sheath. The intraoperative change in procedure can be facilitated by the use of a suturing device that can be easily and securely attached to the scope and changed from a stowed position that facilitates navigation of the scope to a deployed position that facilitates use of the suturing device with the scope. Thus, the devices and methods described herein can expedite medical procedures and facilitate better patient outcomes.

VARIOUS NOTES & EXAMPLES

Example 1 is an electromagnetically driven suturing device comprising: a body; a first coil embedded in the body; and a suturing element configured to be actuated by a magnetic field generated by the first coil.

In Example 2, the subject matter of Example 1 optionally includes the body comprising: a first arm having a first end face; and a second arm having a second end face at least partially opposing the first end face; wherein the first coil is positioned in the first arm such that a central axis of the first coil extends out the first end face.

In Example 3, the subject matter of Example 2 optionally includes the central axis of the first coil extending transverse to a central axis of the scope.

In Example 4, the subject matter of any one or more of Examples 2-3 optionally includes a cap rotatably connected to the base, wherein the cap is configured to mount to the scope.

In Example 5, the subject matter of any one or more of Examples 2-4 optionally includes a biasing element coupled to the suturing element.

In Example 6, the subject matter of any one or more of Examples 2-5 optionally includes a second coil located in the second arm such that a central axis of the second coil extends out the second end face.

In Example 7, the subject matter of Example 6 optionally includes the suturing element being configured to reciprocate between the first coil and the second coil.

In Example 8, the subject matter of Example 7 optionally includes each coil being configured to push and pull the suturing element.

In Example 9, the subject matter of any one or more of Examples 6-8 optionally includes the suturing element being configured to circulate between the first coil and the second coil.

In Example 10, the subject matter of Example 9 optionally includes a third coil, wherein a center of each coil is spaced one-hundred-twenty degrees from other coils.

In Example 11, the subject matter of any one or more of Examples 6-10 optionally includes a controller configured to selectively activate the first and second coils.

In Example 12, the subject matter of any one or more of Examples 6-11 optionally includes a magnet mounted to the suturing element to enhance interaction with the magnetic field.

In Example 13, the subject matter of any one or more of Examples 6-12 optionally includes the suturing element being configured to be directly driven by the magnetic field.

In Example 14, the subject matter of any one or more of Examples 6-13 optionally include the suturing element being indirectly driven by the magnetic field.

In Example 15, the subject matter of Example 14 optionally includes a first shuttle configured to interact with the magnetic field to drive the suturing element.

In Example 16, the subject matter of Example 15 optionally includes the first shuttle comprising: a hammer configured to impact the suturing element.

In Example 17, the subject matter of Example 16 optionally includes the hammer comprising: a mass configured to slide in the first arm; and a tip extending from the mass configured to impact the suturing element.

In Example 18, the subject matter of any one or more of Examples 15-17 optionally includes the first shuttle comprising: a carriage configured to attach to the suturing element.

In Example 19, the subject matter of Example 18 optionally includes the carriage comprising: a socket to receive the suturing element; and a gripper element to secure the suturing element in the socket.

In Example 20, the subject matter of any one or more of Examples 1-19 optionally includes means for immobilizing suture material embedded into tissue by the suturing element.

Example 21 is an electro-magnetic suturing device comprising: a C-shaped housing comprising: a first arm having a first end face; a first suturing track extending into the first end face; a second arm having a second end face at least partially opposing the first end face; a second suturing track extending into the second end face; a first coil embedded in the first arm; and a suturing element configured to be driven by a magnetic field generated by the first coil to move from the first suturing track to the second suturing track.

In Example 22, the subject matter of Example 21 optionally includes the suturing element, the first suturing track and the second suturing track being arcuate.

In Example 23, the subject matter of any one or more of Examples 21-22 optionally include a biasing mechanism attached to the suturing element to oppose a force generated by the magnetic field.

In Example 24, the subject matter of any one or more of Examples 21-23 optionally includes the suturing element comprising a magnet to facilitate engagement with the magnetic field.

In Example 25, the subject matter of any one or more of Examples 21-24 optionally includes the suturing element comprising a coupling feature for suturing material located proximate a center of the suturing element.

In Example 26, the subject matter of any one or more of Examples 21-25 optionally includes the body comprising a second coil embedded in the second arm to facilitate reciprocating of the suturing element.

In Example 27, the subject matter of any one or more of Examples 21-26 optionally includes the body comprising a third coil embedded in the first or second arm to facilitate circulation of the suturing element about the C-shaped housing.

In Example 28, the subject matter of any one or more of Examples 21-27 optionally includes the first suturing track comprising a circular arc segment.

In Example 29, the subject matter of Examples 21-27 optionally includes the first suturing track having a shape of an infinity symbol.

In Example 30, the subject matter of any one or more of Examples 21-29 optionally includes the suturing element comprising barbs to facilitate one way sliding of the suturing element.

Example 31 is an electro-magnetic hammer suturing device comprising: a housing; and a first coil embedded in the housing; a first shuttle configured to be reciprocated in the housing by an electromagnetic field generated by the first coil; and a suturing element configured to be actuated by the first shuttle.

In Example 32, the subject matter of Example 31 optionally includes the housing comprising: a first arm having a first end face, the first coil located in the first arm; a first suturing track extending into the first end face; and a second arm having a second end face at least partially opposing the first end face.

In Example 33, the subject matter of Example 32 optionally includes a second suturing track extending into the second end face; a second coil embedded in the second arm; and a second carriage located in the second suturing track and configured to be actuated by a second magnetic field generated by the second coil.

In Example 34, the subject matter of any one or more of Examples 31-33 optionally includes the first shuttle comprising a hammer configured to impact the suturing element.

In Example 35, the subject matter of Example 34 optionally includes the hammer comprising: a mass configured to slide in the first arm; and a tip extending from the mass configured to impact the suturing element.

In Example 36, the subject matter of any one or more of Examples 31-35 optionally includes the first shuttle comprising a carriage configured to attach to the suturing element.

In Example 37, the subject matter of any one or more of Examples 34-36 optionally includes the carriage comprising: a socket to receive the suturing element; and a gripper element to secure the suturing element in the socket.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An electromagnetically driven suturing device comprising:
  a body;
  a first coil embedded in the body; and
  a suturing element configured to be actuated by a magnetic field generated by the first coil.

2. The electromagnetically driven suturing device of claim 1, wherein the body comprises:
  a first arm having a first end face; and
  a second arm having a second end face at least partially opposing the first end face;
  wherein the first coil is positioned in the first arm such that a central axis of the first coil extends out the first end face.

3. The electromagnetically driven suturing device of claim 2, wherein the central axis of the first coil extends transverse to a central axis of the scope.

4. The electromagnetically driven suturing device of claim 2, further comprising a cap rotatably connected to the base, wherein the cap is configured to mount to the scope.

5. The electromagnetically driven suturing device of claim 2, further comprising a biasing element coupled to the suturing element.

6. The electromagnetically driven suturing device of claim 2, further comprising a second coil located in the second arm such that a central axis of the second coil extends out the second end face.

7. The electromagnetically driven suturing device of claim 6, wherein the suturing element is configured to reciprocate between the first coil and the second coil.

8. The electromagnetically driven suturing device of claim 7, wherein each coil is configured to push and pull the suturing element.

9. The electromagnetically driven suturing device of claim 6, wherein the suturing element is configured to circulate between the first coil and the second coil.

10. The electromagnetically driven suturing device of claim 9, further comprising a third coil, wherein a center of each coil is spaced one-hundred-twenty degrees from other coils.

11. The electromagnetically driven suturing device of claim 6, further comprising a controller configured to selectively activate the first and second coils.

12. The electromagnetically driven suturing device of claim 6, further comprising a magnet mounted to the suturing element to enhance interaction with the magnetic field.

13. The electromagnetically driven suturing device of claim 6, wherein the suturing element is configured to be directly driven by the magnetic field.

14. The electromagnetically driven suturing device of claim 6, wherein the suturing element is indirectly driven by the magnetic field.

15. The electromagnetically driven suturing device of claim 14, further comprising a first shuttle configured to interact with the magnetic field to drive the suturing element.

16. The electromagnetically driven suturing device of claim 15, wherein the first shuttle comprises:
  a hammer configured to impact the suturing element.

17. The electromagnetically driven suturing device of claim 16, wherein the hammer comprises:
  a mass configured to slide in the first arm; and
  a tip extending from the mass configured to impact the suturing element.

18. The electromagnetically driven suturing device of claim 15, wherein the first shuttle comprises:
  a carriage configured to attach to the suturing element.

19. The electromagnetically driven suturing device of claim 18, wherein the carriage comprises:
  a socket to receive the suturing element; and
  a gripper element to secure the suturing element in the socket.

20. The electromagnetically driven suturing device of claim 1, further comprising means for immobilizing suture material embedded into tissue by the suturing element.

21. An electro-magnetic suturing device comprising:
  a C-shaped housing comprising:

a first arm having a first end face;

a first suturing track extending into the first end face;

a second arm having a second end face at least partially opposing the first end face;

a second suturing track extending into the second end face;

a first coil embedded in the first arm; and a suturing element configured to be driven by a magnetic field generated by the first coil to move from the first suturing track to the second suturing track.

22. The electromagnetic suturing device of claim 21, wherein the suturing element, the first suturing track and the second suturing track are arcuate.

23. The electromagnetic suturing device of claim 21, further comprising a biasing mechanism attached to the suturing element to oppose a force generated by the magnetic field.

24. The electromagnetic suturing device of claim 21, wherein the suturing element comprises a magnet to facilitate engagement with the magnetic field.

25. The electromagnetic suturing device of claim 21, wherein the suturing element comprises a coupling feature for suturing material located proximate a center of the suturing element.

26. The electromagnetic suturing device of claim 21, wherein the body comprises a second coil embedded in the second arm to facilitate reciprocating of the suturing element.

27. The electromagnetic suturing device of claim 21, wherein the body comprises a third coil embedded in the first or second arm to facilitate circulation of the suturing element about the C-shaped housing.

28. The electromagnetic suturing device of claim 21, wherein the first suturing track comprises a circular arc segment.

29. The electromagnetic suturing device of claim 21, wherein the first suturing track has a shape of an infinity symbol.

30. The electromagnetic suturing device of claim 21, wherein the suturing element comprises barbs to facilitate one way sliding of the suturing element.

* * * * *